(12) United States Patent
Yencho

(10) Patent No.: US 7,270,670 B1
(45) Date of Patent: *Sep. 18, 2007

(54) MINIMALLY-INVASIVE SURGICAL SYSTEM UTILIZING A STABILIZER

(75) Inventor: Stephen A. Yencho, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 637 days.

This patent is subject to a terminal disclaimer.

(21) Appl. No.: 10/439,382

(22) Filed: May 16, 2003

Related U.S. Application Data

(63) Continuation-in-part of application No. 10/420,551, filed on Apr. 21, 2003.

(51) Int. Cl.
*A61B 17/10* (2006.01)
*A61B 1/32* (2006.01)

(52) U.S. Cl. .................. 606/139; 606/143; 600/207

(58) Field of Classification Search .............. 606/1, 606/139–144, 235, 151–158, 191, 192, 194, 606/198; 600/37, 201–208, 231, 235; 227/175.1–180.1
See application file for complete search history.

(56) References Cited

U.S. PATENT DOCUMENTS

| | | | |
|---|---|---|---|
| 5,104,393 A | 4/1992 | Isner et al. | |
| 5,119,983 A * | 6/1992 | Green et al. | 227/179.1 |
| 5,197,648 A | 3/1993 | Gingold | |
| 5,203,776 A | 4/1993 | Durfee | |
| 5,250,038 A | 10/1993 | Melker et al. | |
| 5,275,622 A | 1/1994 | Lazarus et al. | |
| 5,411,508 A * | 5/1995 | Bessler et al. | 606/153 |
| 5,433,700 A | 7/1995 | Peters | |
| 5,452,733 A | 9/1995 | Sterman et al. | |
| 5,695,504 A * | 12/1997 | Gifford et al. | 606/153 |
| 5,702,412 A | 12/1997 | Popov et al. | |
| 5,727,569 A | 3/1998 | Benetti et al. | |
| 5,735,290 A | 4/1998 | Sterman et al. | |
| 5,782,746 A | 7/1998 | Wright | |
| 5,836,311 A | 11/1998 | Borst et al. | |
| 5,865,730 A * | 2/1999 | Fox et al. | 600/228 |
| 5,885,271 A | 3/1999 | Hamilton et al. | |
| 5,888,247 A | 3/1999 | Benetti | |

(Continued)

FOREIGN PATENT DOCUMENTS

WO 99/21491 5/1999

(Continued)

OTHER PUBLICATIONS

U.S. Appl. No. 10/420,551, filed Apr. 2003, Yencho et al.*

(Continued)

*Primary Examiner*—Glenn K. Dawson
*Assistant Examiner*—Kathleen Sonnett
(74) *Attorney, Agent, or Firm*—Brian A. Schar

(57) ABSTRACT

A minimally-invasive anastomosis system includes a suspension that connects an anastomosis tool to a stabilizer. The stabilizer may be rigidly connected to a retractor or other structure that is fixed relative to the patient. The suspension facilitates anastomosis of a graft vessel to a target vessel in that tissue, by allowing the anastomosis tool to move relative to the stabilizer so that it can move along with the remaining motion of the heart tissue.

22 Claims, 11 Drawing Sheets

U.S. PATENT DOCUMENTS

| | | | |
|---|---|---|---|
| 5,891,017 A | 4/1999 | Swindle et al. | |
| 5,894,843 A | 4/1999 | Benetti et al. | |
| 5,906,607 A * | 5/1999 | Taylor et al. | 606/1 |
| 5,947,896 A | 9/1999 | Sherts et al. | |
| 5,957,835 A | 9/1999 | Anderson et al. | |
| 5,967,972 A * | 10/1999 | Santilli et al. | 600/232 |
| 5,976,080 A | 11/1999 | Farascioni | |
| 6,015,378 A | 1/2000 | Borst et al. | |
| 6,019,722 A | 2/2000 | Spence et al. | |
| 6,026,814 A | 2/2000 | LaFontaine et al. | |
| 6,036,641 A | 3/2000 | Taylor et al. | |
| 6,066,144 A | 5/2000 | Wolf et al. | |
| 6,068,637 A | 5/2000 | Popov et al. | |
| 6,071,295 A | 6/2000 | Takahashi | |
| 6,083,153 A | 7/2000 | Rullo et al. | |
| 6,110,187 A | 8/2000 | Donlon | |
| 6,113,612 A | 9/2000 | Swanson et al. | |
| 6,149,583 A | 11/2000 | Vierra et al. | |
| 6,152,937 A | 11/2000 | Peterson et al. | |
| 6,167,889 B1 | 1/2001 | Benetti | |
| 6,193,652 B1 | 2/2001 | Berky et al. | |
| 6,193,734 B1 | 2/2001 | Bolduc et al. | |
| 6,199,556 B1 | 3/2001 | Benetti et al. | |
| 6,231,585 B1 | 5/2001 | Takahashi et al. | |
| 6,248,119 B1 | 6/2001 | Solem | |
| 6,251,116 B1 | 6/2001 | Shennib et al. | |
| 6,253,769 B1 | 7/2001 | LaFontaine et al. | |
| 6,254,535 B1 | 7/2001 | Furnish et al. | |
| 6,290,644 B1 | 9/2001 | Green, II et al. | |
| 6,296,630 B1 | 10/2001 | Altman et al. | |
| 6,309,349 B1 | 10/2001 | Bertolero et al. | |
| 6,325,067 B1 | 12/2001 | Sterman et al. | |
| 6,331,158 B1 | 12/2001 | Hu et al. | |
| 6,334,843 B1 | 1/2002 | Borst et al. | |
| 6,338,710 B1 | 1/2002 | Takahashi et al. | |
| 6,338,712 B2 | 1/2002 | Spence et al. | |
| 6,346,077 B1 | 2/2002 | Taylor et al. | |
| 6,352,543 B1 | 3/2002 | Cole | |
| 6,354,994 B1 | 3/2002 | Rullo et al. | |
| 6,361,492 B1 | 3/2002 | Santilli | |
| 6,394,948 B1 | 5/2002 | Borst et al. | |
| 6,447,443 B1 * | 9/2002 | Keogh et al. | 600/37 |
| 6,475,222 B1 | 11/2002 | Berg et al. | |
| 6,478,028 B1 | 11/2002 | Paolitto et al. | |
| 6,478,728 B1 | 11/2002 | Wright | |
| 6,494,211 B1 | 12/2002 | Boyd et al. | |
| 6,511,416 B1 | 1/2003 | Green, II et al. | |
| 6,511,491 B2 | 1/2003 | Grudem et al. | |
| 6,537,323 B2 | 3/2003 | Weinstein et al. | |
| 6,626,920 B2 | 9/2003 | Whayne | |
| 6,626,921 B2 * | 9/2003 | Blatter et al. | 606/153 |
| 6,676,597 B2 | 1/2004 | Guenst et al. | |
| 6,758,808 B2 | 7/2004 | Paul et al. | |
| 6,786,898 B2 | 9/2004 | Guenst | |
| 6,818,001 B2 | 11/2004 | Wulfman et al. | |
| 6,869,437 B1 * | 3/2005 | Hausen et al. | 606/153 |
| 6,899,670 B2 | 5/2005 | Peng et al. | |
| 2002/0082470 A1 | 6/2002 | Devries et al. | |
| 2002/0095067 A1 | 7/2002 | Guenst et al. | |
| 2002/0147406 A1 | 10/2002 | von Segesser | |
| 2003/0009182 A1 | 1/2003 | Whayne | |
| 2003/0010346 A1 | 1/2003 | Paolitto et al. | |
| 2003/0078471 A1 | 4/2003 | Foley et al. | |
| 2003/0167064 A1 | 9/2003 | Whayne | |
| 2004/0162570 A1 | 8/2004 | Dave et al. | |
| 2005/0182431 A1 * | 8/2005 | Hausen et al. | 606/153 |
| 2005/0228410 A1 * | 10/2005 | Berreklouw | 606/153 |

FOREIGN PATENT DOCUMENTS

| | | |
|---|---|---|
| WO | 00/56228 | 9/2000 |
| WO | 02/30172 | 4/2002 |
| WO | 2004/064646 A1 | 1/2004 |
| WO | 2004/064647 A1 | 1/2004 |

OTHER PUBLICATIONS

Damiano, Jr. et al, Jan. 2000, Initial US Clinical Trail of Robotically Assisted Endoscopic Coronary Artery Bypass Grafting, pp. 77-82, Journal of Thoracic and Cardiovascular Surgery.

Falk, Volkmar et al, 2000, Total Endoscopic Computer Enhanced Coroanry Artery Bypass Grafting, pp. 38-45, European Journal of Cardio-thoracic Surgery.

Falk, Volkmar et al, Feb. 21, 2000, Total Endoscopic Off-Pump Coronary Artery Bypass Grafting, pp. 29-31, The Heart Surgery Forum.

Tabaie, Harold et al, Sep. 7, 1999, Endoscopic Coronary Artery Bypass Graft Procedure with Robotic Assistance, pp. 1-9, The Heart Surgery Forum.

Falk, Volkmar et al, Jul 7, 1999, Endoscopic Coronary Artery Bypass Grafting on the Beating Heart Using a Computer Enhanced Telemanipulation System, pp. 1/8, The Heart Surgery Forum.

Falk, Volkmar et al, Feb. 21, 2000, Total Endoscopic Off-Pump Coronary Artery Bypass Grafting, pp. 1-4, The Heart Surgery Forum.

Kappert, Utz et al, Jun. 8, 2000, Closed Chest Coronary Artery Bypass on the Beating Heart, pp. 1-4, The Heart Surgery Forum.

Farrar, David, Jan. 13, 2000, Development of a Prosthetic Coronary Artery Bypass Graft, pp. 1-6, The Heart Surgery Forum.

Falk, Volkmar et al, Jun. 24, 2000, Endoscopic Doppler for Detecting Vessels in Closed Chest Bypass Grafting, pp. 1-5, The Heart Surgery Forum.

Zamvar, Vipin, et al, Nov. 30, 2000, Bleeding from the Lung Surface: A Unique Complication of Off-Pump CABG Operation, pp. 1-2, The Heart Surgery Forum.

Loulmet, Didier et al, Jul. 1999, Endoscopic Coronary Artery Bypass Grafting with the Aid of Robotic Assisted Instruments, pp. 4-10, The Journal of Thoracic and Cardiovascular Surgery.

Falk, V et al, 1999, Quality of Computer Enhanced Totally Endoscopic Coronary Bypass Graft Anastomosis, pp. 260-265, European Journal of Cardio-thoracic Surgery.

Mohr, Friedrich et al, May 2001, Computer-Enhanced "Robotic" Cardiac Surgery: Experience in 148 Patients, pp. 842-853, The Journal of Thoracic and Cardiovascular Surgery.

Boyd, W et al, Jan. 31, 2000, A Comparison of Robot-Assisted Versus Manually Constructed Endoscopic Coronary Anastomosis, pp. 1-9, The Annals of Thoracic Surgery.

Korkola, S et al, 2000, A Novel Automated Interrupted Suturing Device for Coronary Artery Bypass Grafting, Abstract, The Heart Surgery Forum.

Morota, T et al, 2000, Proximal One-Shot Anastomotic Device: Short-Term Results, Abstract, The Heart Surgery Forum.

Matheny, Robert, 1999, A Perspective on MIDCAB, Editorial, Heart Surgery Forum.

Mandke, NV et al, 2000, Three Year Follow Up of Minimally Invasive Coronary Artery Surgery, Abstract, Heart Surgery Forum.

1999, Off-Pump Coronary Artery Bypass Surgery: Wave of the Future, Article, www.ccf.org.

Solem, Jan et al, Mar. 1, 2000, European Journal of Cardio-Thoracic Surgery, Abstract, European Journal of Cardio-Thoracic Surgery.

Boyd, W et al, Oct. 2000, Closed-Chest Coronary Artery Bypass Grafting on the Beating Heart with the Use of a Computer-Enhanced Surgical Robotic System, pp. 807-809, The Journal of Thoracic and Cardiovascular Surgery.

Kappert, Utz et al, Oct. 2000, Closed-Chest Coronary Artery Surgery on the Beating Heart with the Use of a Robotic System, pp. 809-811, The Journal of Thoracic and Cardiovascular Surgery.

Reichenspurner, Hermann et al, Nov. 1999, Robotically Assisted Endoscopic Coronary Artery Bypass Procedures Without Cardiopulmonary Bypass, pp. 1-4, The Journal of Thoracic and Cardiovascular Surgery.

Falk, Volkmar et al, 2000, Total Endoscopic Computer Enhanced Coronary Artery Bypass Grafting, pp. 1-15, European Journal of Cardio-Thoracic Surgery.

Boyd, W et al, Feb. 2001, RAVECAB: Improving Outcome in Off-Pump Minimal Access Surgery with Robotic Assistance and Video Enhancement, pp. 45-50, Canadian Journal of Surgery.

Chiu, Adeline et al, Jun. 8, 2000, 3-D Image Guidance for Minimally Invasive Robotic Coronary Artery Bypass, pp. 224-231, The Heart Surgery Forum.

Kiaii, Bob et al, May 28, 2000, Robot-Assisted Computer Enhanced Closed-Chest Coronary Surgery, pp. 194-197, The Heart Surgery Forum.

Kappert, Utz et al, Jan. 27, 2000, Wrist-Enhanced Instrumentation: Moving Toward Totally Endoscopic Coronary Artery Bypass Grafting, pp. 1-8, The Annals of Thoracic Surgery.

Kappert, Utz et al, 2000, Closed Chest Bilateral Mammary Artery Grafting in Double-Vessel Coronary Artery Disease, pp. 1-4, The Annals of Thoracic Surgery.

Cichon, Romuald et al, Jan. 27, 2000, Robotic-Enhanced Arterial Revascularization for Multivessel Coronary Artery Disease, pp. 1060-1062, The Annals of Thoracic Surgery.

Kappert, Utz et al, Jun. 8, 2000, Robotic-Enhanced Dredsden Technique for Minimally Invasive Bilateral Internal Mammary Artery Grafting, pp. 319-321, The Heart Surgery Forum.

Tabaie, Harold et al, Sep. 7, 1999, Endoscopic Coronary Artery Bypass Graft Procedure with Robotic Assistance, pp. 310-316, The Heart Surgery Forum.

Damiano, Ralph et al, Jan. 2000, Initial US Clinical Trial of Robotically Assisted Endoscopic Coronary Artery Bypass Grafting, pp. 77-82, The Journal of Thoracic and Cardiovascular Surgery.

US 6,503,260, 01/2003, Schaller et al. (withdrawn)

* cited by examiner

US 7,270,670 B1

MINIMALLY-INVASIVE SURGICAL SYSTEM UTILIZING A STABILIZER

This application is a continuation-in-part of U.S. patent application Ser. No. 10/420,551, filed on Apr. 21, 2003.

FIELD OF THE INVENTION

The present invention relates generally to anastomosis, and more particularly to minimally-invasive anastomosis.

BACKGROUND

A coronary artery bypass graft (CABG) procedure is a common surgical procedure in which a graft vessel, such as a saphenous vein or mammary artery, is connected surgically to a target vessel, or between two target vessels. Typically, the patient's chest is opened in order to perform this procedure, whether it is performed as a stopped-heart or beating-heart procedure. Opening the chest creates a major trauma from which it takes the patient some time to heal. Additionally, the patient is left with a large scar, and may have lasting pain. Attempts have been made to perform the CABG procedure in a minimally-invasive manner, using tools inserted through incisions in the thoracic cavity and/or percutaneously. However, such attempts have not met with significant acceptance by cardiac surgeons, due to problems inherent in the previous minimally-invasive procedures. One problem is that such procedures may utilize traditional rigid stabilizers that immobilize a portion of the heart, such as by pressing down on it or lifting up a portion of the surface, such that the heart cannot move freely during the anastomosis procedure. Rigid stabilizers are fixed rigidly to a retractor or other structure that itself is substantially fixed. However, fibrillation often results from such attempts to immobilize a portion of the heart. Fibrillation complicates the CABG procedure at best and is potentially fatal at worst. Another problem is that robotic devices that may be used for minimally-invasive surgery are expensive capital goods that some hospitals may not be able to afford. Such robotic devices may be capable of compensating for the motion of the heart by using software that measures the motion of the heart and adds a motion component to a robotic manipulator that cancels out at least some of the motion of that manipulator relative to the heart. However, such compensation is complex, and adds to the complexity and expense of the robotic device. Further, the manipulators used to perform the surgery are typically complex and expensive. As a result of the complexity of the robotic devices, surgeons typically require a significant amount of training time on them to become proficient, time which takes them away from their practices.

SUMMARY

In one aspect of the invention, a suspension connects an anastomosis tool to a stabilizer. The stabilizer may be rigidly connected to a retractor or other structure that is fixed relative to the patient. The stabilizer may be introduced into the thoracic cavity of a patient via an intercostal incision, a sub-xyphoid incision, or a differently-located incision. Where the stabilizer is placed against heart tissue, the heart tissue in contact with that stabilizer is substantially immobilized. However, tissue in proximity to the stabilizer may still move a small amount. The suspension facilitates anastomosis of a graft vessel to a target vessel in that tissue, by allowing the tool to move relative to the stabilizer so that it can move along with the remaining motion of the heart tissue.

In another aspect of the invention, the tool includes an anvil and a staple holder movable relative to one another. The anvil is movable relative to the stabilizer, where that motion includes at least one rotational component. By pivoting relative to the stabilizer, the anvil can be steered to an orientation in which it is substantially aligned with a target vessel.

In another aspect of the invention, the tool is movable relative to the stabilizer, where that motion is at least partly in a direction toward the target vessel, such that the anvil can penetrate the target vessel. After insertion of a portion of the anvil into the lumen of the target vessel, the suspension allows the anvil to float relative to the stabilizer. As a result, where the target vessel is a coronary artery and the heart is beating, the anvil does not tear or otherwise damage the coronary artery after insertion into the lumen thereof.

BRIEF DESCRIPTION OF THE DRAWINGS

The use of the same reference symbols in different figures indicates similar or identical items.

DETAILED DESCRIPTION

Figure 1:
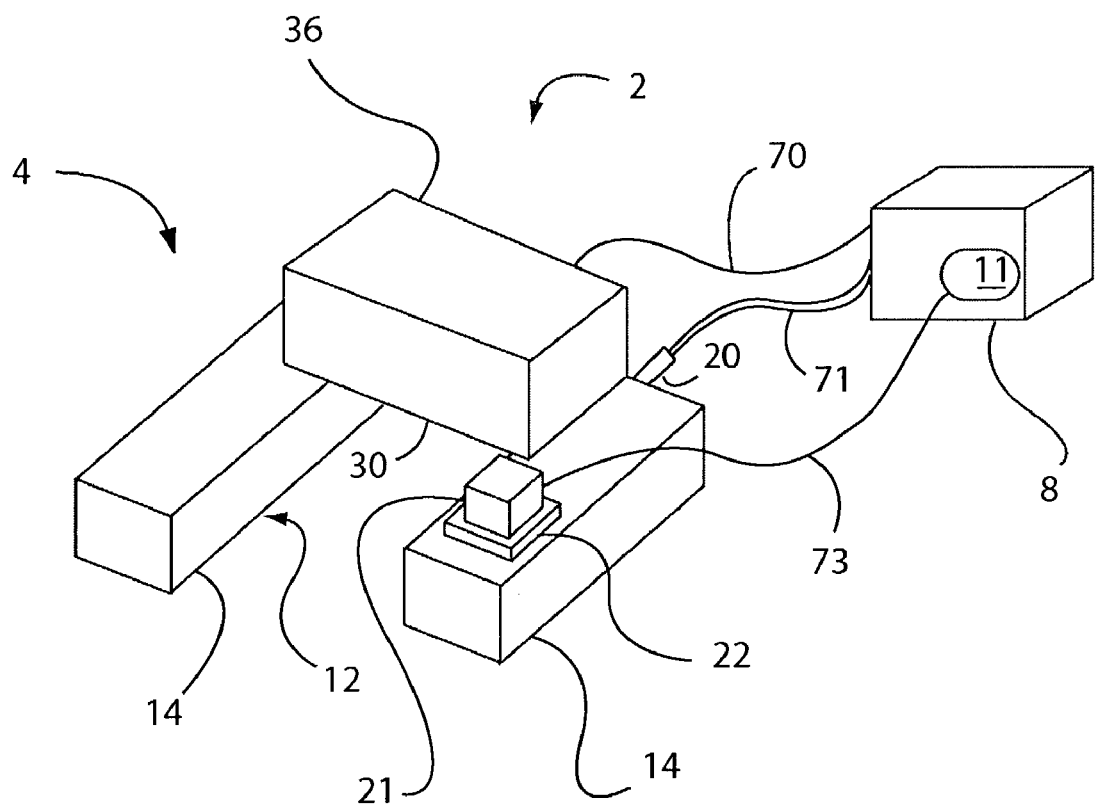
FIG. 1 is a schematic view of a minimally-invasive surgical system.

Referring to FIG. 1, a schematic view of a minimally-invasive surgical system 2 is shown. The surgical system 2 includes an effector 4 configured to engage tissue. The effector 4 includes a base 12 that is configured to be attached to tissue, such as by suction, while allowing substantially unrestricted motion of that tissue. The tissue may be heart tissue, such that the base 12 is configured for attachment to the exterior of the heart while allowing the heart to move substantially freely during the duration of that attachment. As used in this document, the term "heart" may refer to the heart itself, as well as the heart in combination with one or more layers of tissue that are present on its exterior, such as the epicardium, pericardium, myocardium, coronary arteries and/or fatty tissue. The base 12 may be at least partially flexible, and/or substantially conformable to the heart. For example, the base 12 may be composed at least partially of silicone. The base 12 shown in FIG. 1 is merely exemplary; the base 12 can be shaped in any appropriate manner. The base 12 may be unitary, have multiple independent components, or have a uniform cross-section or a cross-section that varies over at least a part of the base 12. The base 12 may be symmetrical, at least in part, or asymmetrical. Optionally, the effector 4 may be detachable from the remainder of the system 2, such that effectors 4 may be interchanged on the system. This interchangeability allows the system to be used for multiple procedures on the same patient.

The base 12 may include one or more contact elements 14 that are configured to contact tissue, such as heart tissue. The contact element or elements 14 may form the entire base 12, or may be connected to a frame and/or other structure (not shown) to form the base 12. Where multiple contact elements 14 are used, they may be spaced apart from one another, arranged symmetrically about a point or axis, arranged asymmetrically, arranged substantially linearly and/or parallel to one another, or otherwise oriented and/or configured. At least one contact element 14 may be sized and/or shaped differently from at least one other contact element 14.

Figure 3:
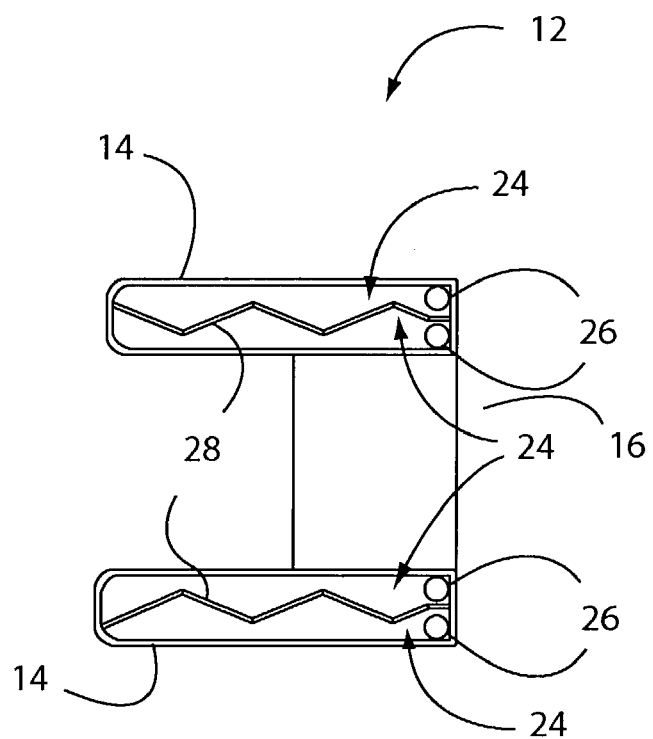
FIG. 3 is a bottom view of the base of FIG. 2.

Referring also to FIG. 3, an example of the underside of one possible configuration of the base 12 is shown. This exemplary base 12 includes two contact elements 14 spaced apart from one another. The contact elements 14 are spaced apart from one another by a distance at least as wide as the maximum width of the average coronary artery. The contact elements 14 are substantially rectangular, and are substantially the same size and shape as one another. However, the contact elements 14 may be shaped in a different manner. For example, the contact elements 14 may have one or more rounded ends, or may be shaped elliptically, trapezoidally, or in a different way. Further, the contact elements 14 need not be the same size and shape as one another. The contact elements 14 may be at least partially flexible. For example, the contact elements 14 may be fabricated from silicone or other flexible biocompatible material. Alternately, the contact elements 14 may be fabricated at least in part from rigid biocompatible material such as stainless steel. Alternately, more than two contact elements 14 may be used. Alternately, a single contact element 14 may be used, with at least two spaced-apart segments. Such a single contact element 14 may have a "U" shape or similar shape.

The contact elements 14 are connected to one another by a bridge 16. The bridge 16 may be formed integrally with the contact elements 14 to form a one-piece unitary structure, or may be connected to the contact elements 14 via adhesive, connectors, or any other appropriate structure, mechanism or method. The bridge 16 allows the contact elements 14 to move relative to one another. For example, the bridge 16 may be formed from silicone or other flexible biocompatible material, such that it can flex and allow the contact elements 14 to move. This motion allows the contact elements 14 to be placed in substantial contact with the exterior of the heart 10. Alternately, the bridge 16 may be made from stainless steel or other rigid biocompatible material, and connected to at least one contact element 14 by a hinge or other mechanism that allows motion of at least one contact element 14 relative to the bridge 16 and/or at least one other contact element 14.

Figure 2:
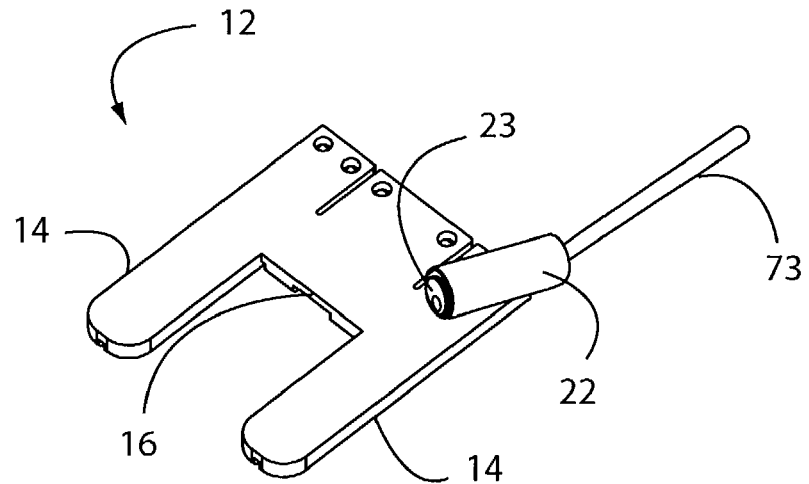
FIG. 2 is a perspective view of a base of an effector used in the system of FIG. 1.

Each contact element 14 includes at least one chamber 24 defined therein, and is substantially open on its underside. The use of the terms "under," "underside," "lower," and "upper" in this document do not limit the orientation in which the effector 4 or other elements of the surgical system 2 may be used, but rather are utilized for convenience and clarity in describing the structure of the surgical system 2. As shown in FIG. 2A, each contact element 14 has an underside that is completely open. However, at least one contact element 14 may have a lower surface that is partially open. For example, the lower surface of at least one contact element 14 may be a smooth plane having one or more apertures or holes defined therein. As another example, the lower surface of at least one contact element 14 may be a screen or mesh. The contact element 14 may have any other suitable configuration of underside or lower surface.

At least one contact element 14 may have more than one chamber 24 defined therein. If so, one or more dividers 28 may separate those chambers 24 from one another. Each divider 28 may extend downward from the upper surface of the corresponding contact element 14, and may be formed integrally with that contact element 14. Each divider 28 is oriented substantially longitudinally along the corresponding contact element 14. Alternately, at least one divider 28 is oriented in a different manner relative to the corresponding contact element 14. The divider 28 has a zig-zag or sawtooth shape. However, at least one divider 28 may be shaped differently. For example, at least one divider 28 may be substantially linear, or substantially curved. The dividers 28 within different contact elements 14 and/or the same contact element 14 may be shaped and/or oriented differently from one another.

At least one connector 20 is attached to or formed integrally with at least one contact element 14. The connector 20 is used to connect the corresponding contact element 14 to a vacuum source. Thus, the connector 20 may be any connector suitable for this purpose. As one example, referring also to FIG. 1, the connector 20 may be a simple pass-through, threaded or not, suitable for connection to a vacuum hose 71. Alternately, the connector 20 is not used. Instead, a port or aperture is provided in at least one contact element 14, where vacuum is applied in another manner to that port or aperture. Vacuum may be provided independently to two or more different chambers 24 in the base 12, thereby providing redundancy in the event that one chamber 24 does not secure to tissue or becomes unsecured from tissue. Further, vacuum may be provided independently to two or more different contact elements 14, providing redundancy in the event that vacuum fails in an entire contact element 14; if so, the remaining contact element or elements 14 can still secure to tissue. An orifice (not shown) may be provided for each chamber 24, sized and positioned to restrict flow into and out of that chamber 24. In this way, any loss of vacuum in one chamber 24 does not substantially propagate back to the vacuum source and result in a loss of vacuum for the other chambers 24 supplied by that vacuum source.

Optionally, at least one contact element 14 includes a bay (not shown) that is thicker than the remainder of the contact element 14, where at least one connector 20 is attached to or extends from the bay. The bay provides additional thickness at an area of the contact element 14, where the connector or connectors 20 that are attached to the bay 20 are large enough to require such additional thickness for adequate mounting to the contact element 14. At least one bay includes a chamber therein that is connected to at least one chamber 24 in the corresponding contact element 14 by a port 26 defined in a surface of that chamber 24. That is, vacuum is applied to each chamber 24 by at least one port 26 defined through a surface of that chamber 24.

The effector 4 may include at least one sensor 21. The sensor 21 is oriented such that it has a view of the area of tissue to be surgically treated, which may be referred to as the surgical field. The sensor 21 may be any type of sensing device, or a component of a larger sensing device. The sensor 21 may be connected to the base 12 and/or to a different part of the effector 4, directly or indirectly. The sensor 21 may be connected to the base 12 and/or other part of the effector 4, in a detachable or a permanent way. The sensor 21 is substantially fixed relative to the base 12. The sensor 21 may be a type that is configured to detect electromagnetic radiation in the visible light portion of the spectrum, such as an endoscope, a camera, or any other type of imaging sensor. Alternately, the sensor 21 may be a part or component of an imaging sensor, such as a CCD chip, a lens or lens assembly, fiber optic cables, or other component of an imaging sensor. Alternately, the sensor 21 may instead or additionally be of a type configured to detect electromagnetic radiation outside the visible light portion of the spectrum, such as an infrared sensor, an ultraviolet sensor or other sensor. An infrared sensor may be useful in detecting the precise location of a coronary artery and/or of a blockage in a coronary artery, because blood flow through the coronary artery and blockage of the coronary artery typically have different temperatures from one another and from surrounding tissue. Alternately, any other sensor that is useful in detecting contrast between a blocked area and an unblocked area of a coronary artery, or between a coronary artery and the remainder of the heart, may be used. Alternately, the sensor 21 itself, or a separate emitter (not shown) emits energy that is modulated or otherwise altered by its interaction with tissue, and the modulated or altered energy is sensed by the sensor 21. For example, such a sensor 21 may be an ultrasound array that emits ultrasonic energy and detects the ultrasonic energy that is reflected from tissue. More than one sensor 21 may be connected to the base 12, if desired. For example, an endoscope and an infrared sensor both may be connected to the base 12.

Sensor data is transmitted from each sensor 21 to a display or similar device that is viewable by the surgeon. This sensor data may be handled in any suitable manner. A display 11 may be included in a control unit 8 connected to the sensor 21, as described in greater detail below. The connection between each sensor and the display 11 may be made through a wire 73, or through a wireless connection. Standard components such as video interface cards, switches, and/or other equipment may be provided between the sensor 21 and the display 11, as is standard in the art. Where multiple sensors 21 are used, each may be connected to the same display 11, and the sensor output may be shown on that display with a split screen, by switching between inputs, or in any other manner. Alternately, the control unit 8 includes output connectors (not shown) that are connectable to a monitor, an information handling system, or other device. If so, the control unit 8 need not include the display 11; rather, sensor data can be passed through the control unit 8 to a monitor of the user's choice; in this way, the control unit 8 can be made smaller and less complex. However, the control unit 8 may contain at least one display 11 and at least one set of output connectors. Alternately, the control unit 8 includes a wireless transmitter that is configured to transmit sensor data from the control unit 8 to another device, such as a monitor or an information handling system. Alternately, sensor data is transmitted directly from the sensor 21 to a display that is unconnected to the control unit, such as by one or more cables or by wireless transmission.

Optionally, the effector 4 includes a sensor mount 22 to which at least one corresponding sensor 21 is connected. The sensor mount 22 is oriented in a direction that provides the corresponding sensor or sensors 21 with a view of the surgical field, as described in greater detail below. Advantageously, the sensor mount 22 is fixed to the base 12. Each sensor 21 may be connected to the corresponding sensor mount 22 in a detachable or a permanent way. The sensor mount 22 is shaped in any appropriate manner to hold a sensor 21 substantially fixed relative to the base 12. Further, the connection between the sensor mount 22 and the corresponding sensor 23 may be accomplished by any appropriate structure, mechanism or method. As an example, where the sensor 21 is an endoscope with a cylindrical body, the sensor mount 22 may be a tubular element configured to hold at least a portion of that cylindrical body via a friction fit or other fit. As another example, the sensor 21 may screw into threads provided on the sensor mount 22. As another example, the sensor 21 may be fixed to the sensor mount 22 with adhesive. As another example, the sensor 21 may be welded or otherwise permanently fixed to the sensor mount 22.

The base 12 is configured to contact tissue, such as by one or more contact elements 14. The contact elements 14 and/or other components of the base 12 are substantially secured to the tissue that they contact, while allowing that tissue to move. That is, the base 12 is connected to and rides on the surface of moving tissue, without substantially restricting the motion of that tissue. For example, the contact elements 14 of the base 12 may be secured to the exterior of the heart, while allowing the heart to beat substantially normally.

The effector 4 includes a tool 36 that is connected to the base 12. The tool 36 may be connected to the base 12 directly, or indirectly via a mount 30. The mount 30 may be any structure or mechanism that is appropriate for holding and/or moving the tool 36 relative to a remainder of the effector 4. The tool 36 is a surgical structure or mechanism that is configured to interact with the tissue to which the base 12 may be connected, or other tissue. Advantageously, the tool 36 is movable relative to the base 12 in at least one degree of freedom. However, the tool 36 may be rigidly connected to the base 12, or may be formed along with the base 12 as a single, integral unit. The tool 36 may be connected to the control unit 8, such as by one or more cables 70. However, the tool 36 may be connected to the control unit 8 indirectly, such as through a cable extending between the base 12 and the control unit 8. Alternately, the tool 36 is operationally connected to the control unit 8 via standard wireless communication hardware and protocols. Optionally, at least one sensor 21 may be connected to the tool 36, instead of or in addition to being connected to the base 21.

The effector 4 as a whole is connected to the control unit 8 non-rigidly. That is, the mechanism or mechanisms, or structure or structures, between the effector 4 and the control unit 8 are non-rigid. Such mechanisms and structures may include cables, hoses, flexible tubes and/or other flexible entities. Thus, the effector 4 is not rigidly connected to any portion of the body of the patient. Because the effector 4 is connected to the control unit 8 non-rigidly, the connection between the effector 4 and the control unit 8 substantially does not restrict any moving tissue to which the effector 4 may be attached. As a result, the effector 4 does not immobilize moving tissue to which it is attached.

The control unit 8 may be used to position and operate the effector 4. The control unit may include a joystick, handle, dial, lever, switch, trigger, console, information handling system such as a computer, a combination of one or more of those mechanisms, or any other appropriate structure, mechanism or combination thereof. The control unit 8 may control the effector 4 mechanically, such as via cables or other force transmission members; electrically and/or via software commands, such as via analog signals or digital commands transmitted to stepper motors or other actuators; by a combination of mechanical and/or electrical devices, and/or software commands, or by another or additional type of mechanism and/or structure.

The tool 36 may be steerable relative to the base 12. That is, the orientation of the tool 36 relative to the base 12 may be controlled, such as via the control unit 8. Further, the position of the tool 36 on the base 12 may be controllable as well, such as via the control unit 8. Thus, the tool 36 may be steered remotely via the control unit 8. A surgeon may utilize the image data or other data transmitted from the sensor 21 to the display 11 to steer the tool 36 within the surgical field such that it engages tissue more effectively for surgical intervention.

The tool 36 may be an anastomosis tool. That is, the tool 36 may be configured to connect a graft vessel to a target vessel, such as by deploying a plurality of staples, clips or other independent connectors, or a unitary anastomosis device. The connector or connectors deployed by the tool 36 may be plastically deformable, superelastic, elastic, or a combination thereof. The anastomosis tool may include an anvil, a delivery mechanism for a unitary connector, a delivery mechanism for a number of separate and independent connectors, and/or any other appropriate mechanism. Further, the anastomosis tool may be configured to perform an arteriotomy on the target vessel before or after deployment of an anastomosis connector or connectors.

Figure 4:
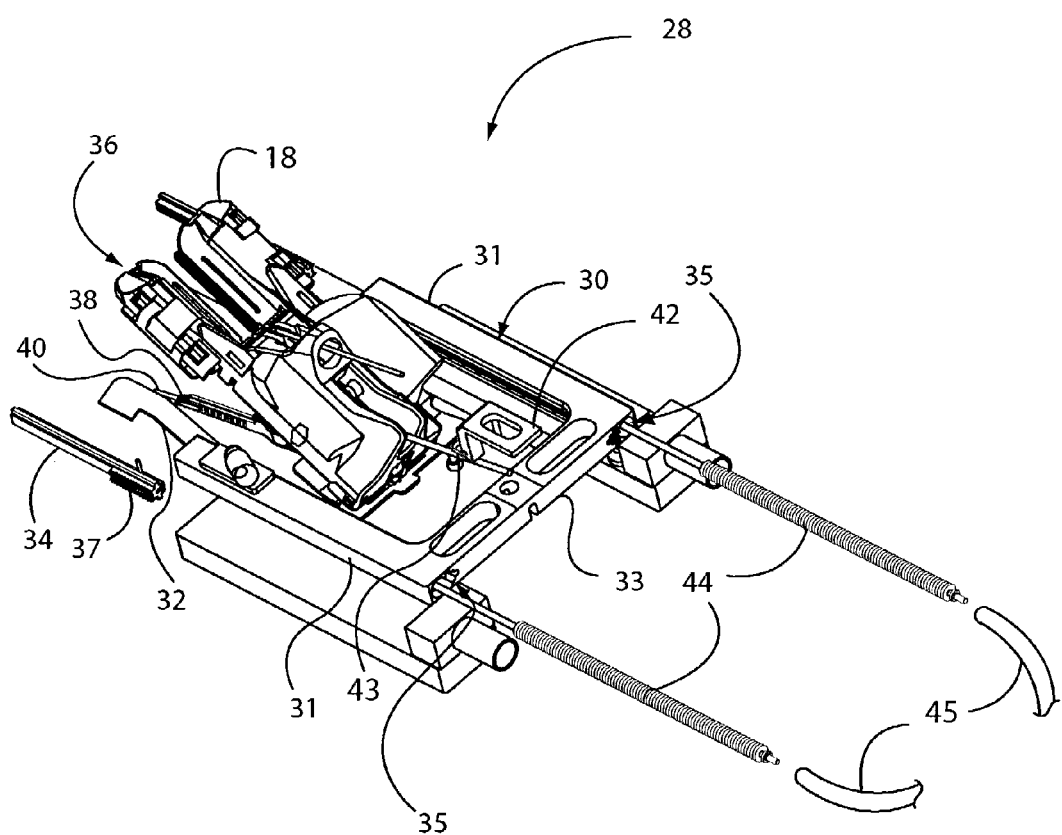
FIG. 4 is a perspective partially-exploded view of a portion of an exemplary effector used in the system of FIG. 1.

Referring also to FIG. 4, an exemplary embodiment of the effector 4 is shown. The effector 4 of FIG. 4 is configured to perform anastomosis, such as a CABG procedure, on moving tissue such as a beating heart 10. As used in this document, the term "heart" may refer to the heart itself, as well as the heart in combination with one or more layers of tissue that are present on its exterior, such as the epicardium, pericardium, and/or fatty tissue. The control unit 8 is located outside of the body of the patient, and the interface extends through a port (not shown) in the chest of the patient. The control unit 8 is connected to the effector 4 via one or more force and/or information transmission mechanisms, which are described in greater detail below.

The base 12 is substantially as described above. A tool 36 is connected to the base 12, where the tool 36 is an anastomosis tool 36. The anastomosis tool 36 may be any appropriate mechanism for deploying one or more anastomosis devices. The anastomosis tool 36 may deploy a unitary anastomosis device, one or more clips, one or more staples, a combination thereof, or a different type of anastomosis device. Alternately, the anastomosis tool 36 is a suturing mechanism or an assisted suturing mechanism. The anastomosis tool 36 may be as described in U.S. patent application Ser. No. 10/151,441 filed on May 20, 2002, "System for Performing Anastomosis" and/or U.S. patent application Ser. No. 10/392,336 filed on Mar. 19, 2003, "System for Performing Anastomosis", both of which are hereby incorporated by reference in their entirety. However, a different anastomosis tool 36 may be utilized, if desired. The anastomosis tool 36 may be configured to hold and deploy at least one staple to connect a graft vessel to a target vessel. The staple or staples may be as described in U.S. patent application Ser. No. 10/309,519 filed on Dec. 4, 2002, "Anastomosis Staple," which is hereby incorporated by reference in its entirety. Alternately, the anastomosis tool 36 may be configured to deploy one or more clips to connect a graft vessel to a target vessel. As one example, such clips may be as described in U.S. Pat. No. 6,193,734 to Bolduc et. al. As another example, such clips may be as described in U.S. Pat. No. 6,503,260 to Schaller et. al. Alternately, the anastomosis tool may be configured to deploy a unitary anastomosis device to connect a graft vessel to a target vessel. As one example, such a unitary anastomosis device may be as described in U.S. patent application Ser. No. 10/057,795, "Integrated Anastomosis System," filed on Jan. 7, 2002, which is hereby incorporated by reference in its entirety. As another example, such a unitary anastomosis device may be as described in U.S. Pat. No. 5,695,504 to Gifford III et. al. As another example, such a unitary anastomosis device may be as described in U.S. Pat. No. 6,152,937 to Peterson et. al. As another example, such a unitary anastomosis device may be as described in U.S. Pat. No. 6,113,612 to Swanson et. al. As another example, such a unitary anastomosis device may be as described in U.S. Pat. No. 6,511,491 to Grudem et. al. As another example, such a unitary anastomosis device may be as described in International Publication No. 00/56228 of Loshakove et. al. As another example, such a unitary anastomosis device may be as described in U.S. Pat. No. 6,251,116 to Shennib et. al. As another example, such a unitary anastomosis device may be the Symmetry device of St. Jude Medical or the CorLink device of Johnson & Johnson. Alternately, the anastomosis tool may be configured to deploy a multi-piece anastomosis device to connect a graft vessel to a target vessel. As one example, such a multi-piece anastomosis device may be as described in U.S. Pat. No. 6,352,543 to Cole. As another example, such a multi-piece anastomosis device may be as described in U.S. Patent Application Publication No. 2003/0023252 of Whayne. As another example, such a multi-piece anastomosis device may be as described in International Publication No. 02/30172 of Loshakove et. al.

For the purpose of illustrating the effector 4 and its operation, the anastomosis tool 36 described below is substantially as disclosed in U.S. patent application Ser. No. 10/392,336, "System for Performing Anastomosis." Such an anastomosis tool 36 includes an anvil 38 configured to penetrate the wall of a target vessel, such as a coronary artery.

Figure 5:
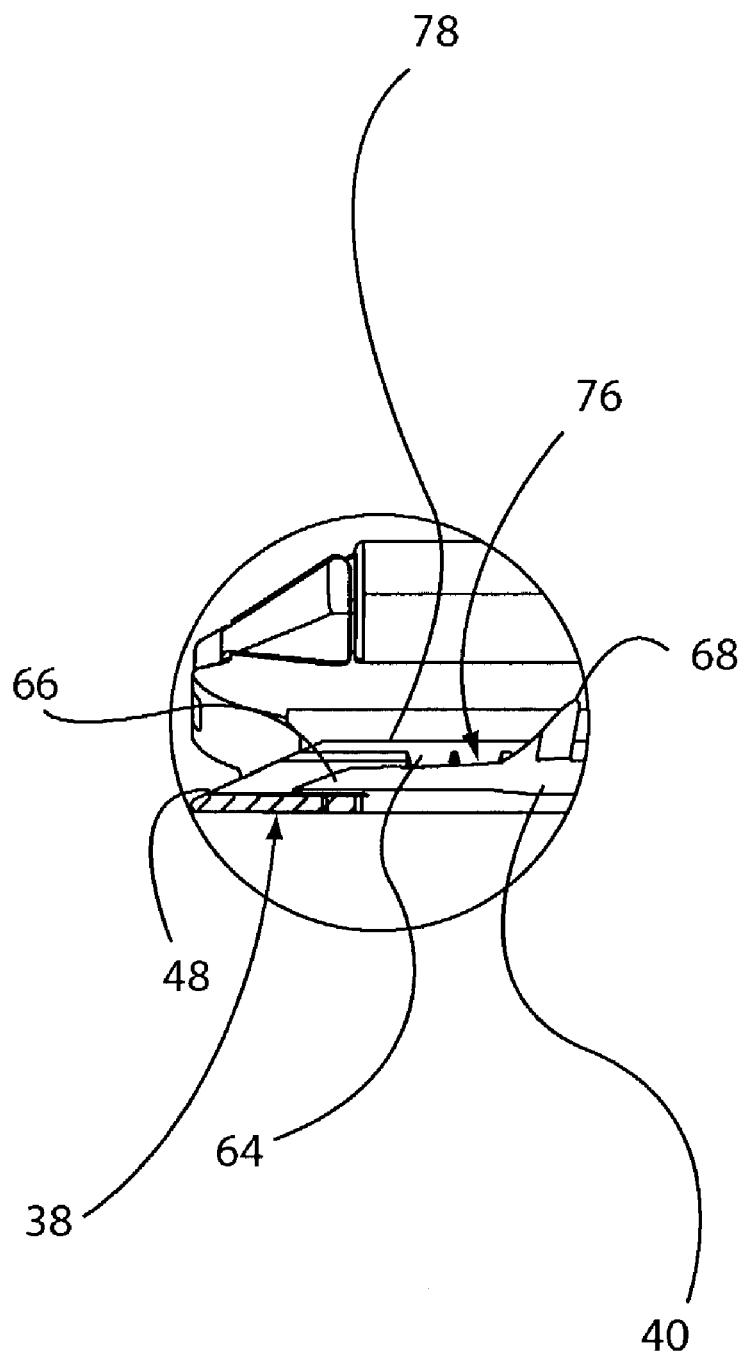
FIG. 5 is a detail view of the distal end of an anvil of FIG. 4.

Referring also to FIG. 5, a cutter 40 is movable relative to the anvil 38. The cutter 40 translates along a channel 64 in the anvil 38. The cutter 40 includes a first incising element 66 at its distal end, and a second incising element 68 on its upper surface. For convenience, the direction substantially perpendicular to the longitudinal centerline of the anvil 38 toward the wall of the target vessel may be referred to as "upward", and the direction substantially perpendicular to the longitudinal centerline of the anvil 38 away from the wall of the target vessel may be referred to as "downward". However, the positioning of the anvil 38 in use is not limited to an orientation in which these directions correspond to absolute directions measured relative to the ground. Similarly, for convenience, motion upward or downward may be referred to as "vertical" motion, and motion substantially parallel to the longitudinal centerline of the anvil arm 14 may be referred to as "horizontal" motion. The second incising element 68 may be spaced apart from and proximal to the first incising element 66. Optionally, the second incising element 68 includes a proximally-facing cutting edge (not shown) to facilitate the creation of an arteriotomy in the wall of the target vessel. The anvil 38 may include an opening 48 at its distal end through which the first incising element 66 extends initially, in order to penetrate the wall of the target vessel. In addition, the anvil 38 includes an upper opening 76 in its upper surface 78 through which the second incising element 68 can be moved to create an arteriotomy in the wall of the target vessel. The arteriotomy is spaced apart from the location at which the anvil 38 penetrates the wall of the target vessel.

Figure 8:
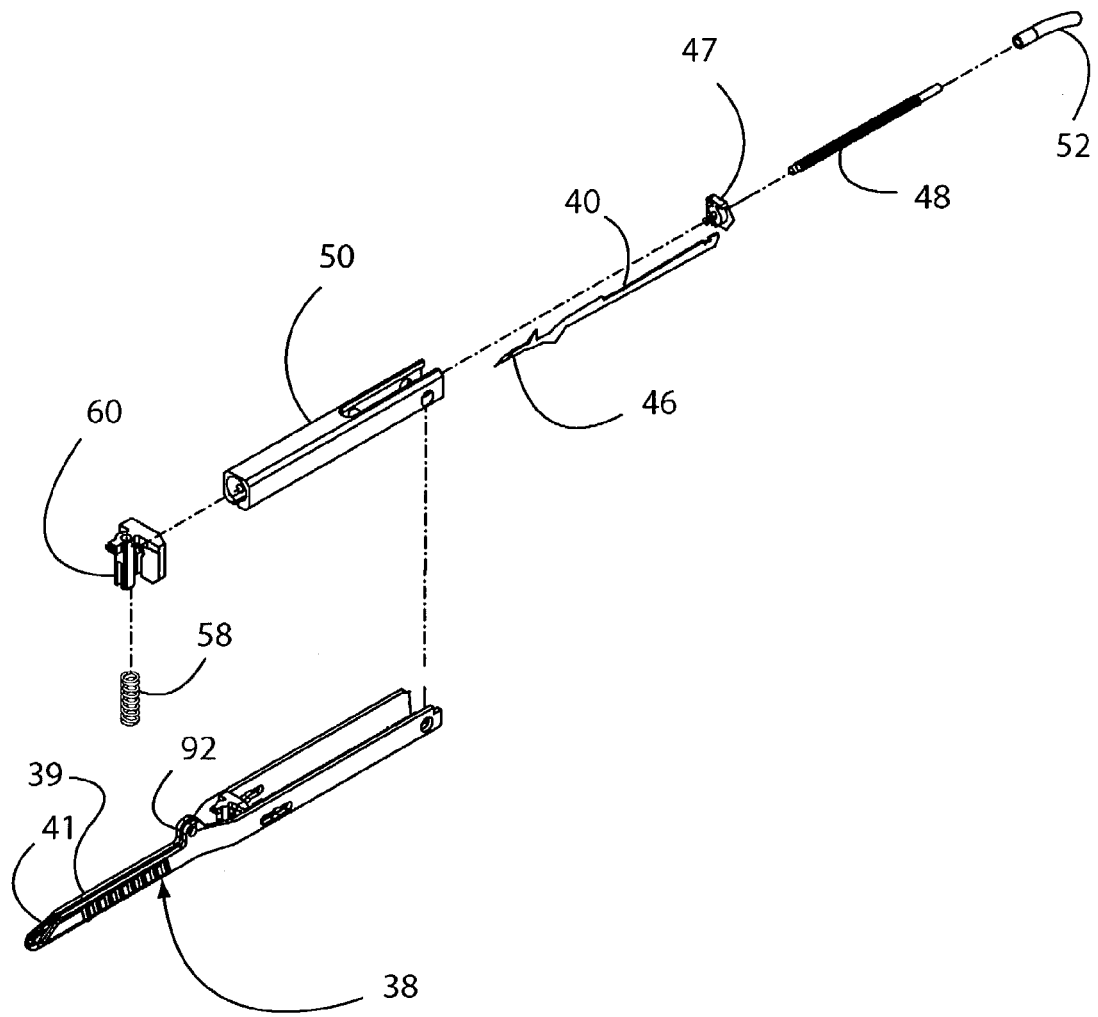
FIG. 8 is an exploded view of the anvil of FIG. 4 and connected structure.

Referring also to FIG. 8, the distal portion of the anvil 38 includes an anvil arm 39 for insertion into the lumen of the target vessel. The cross-sectional area of the anvil arm 39 is small enough such that withdrawal of the anvil arm 39 from the wall of the target vessel substantially does not result in leakage through that wall. The distal tip of the anvil arm 39 may be sharp in order to facilitate penetration of the wall of the target vessel. Also, or instead, the cutter 40 has a sharp distal end 46, and the distal end of the anvil 39 has an aperture 41 therein that allows the distal end 46 of the cutter 40 to protrude outward through the aperture 41 and penetrate the wall of the target vessel.

A stop 92 is located on the anvil 38, at the proximal end of the anvil arm 39. The stop 92 extends upward from the anvil 38 to increase its cross-sectional area, such that the anvil arm 39 substantially cannot penetrate the wall of the target vessel any further than the position defined by the stop 92. The stop 92 is substantially blunt, such that its contact with the wall of the target vessel is substantially atraumatic and substantially does not increase the size of the incision made in the wall of the target vessel by the anvil arm 39.

The anvil 38 includes a widened segment 56 at its proximal end, which is wider than the anvil arm 39. Alternately, the widened segment 56 is no wider than the anvil arm 39. The widened segment 56 may be open along at least a portion of its length. A driver 48 is configured to be positioned at least partly within the widened segment 56. Optionally, the driver 48 is held at least partly within a guide 50 that also is located at least partly within the widened segment 56. The driver 48 is a threaded rod or screw; where the guide 50 is used, that guide 50 is threaded to match. Alternately, the driver 48 is unthreaded, and is configured to be urged relative to the anvil 38 under the influence of compressed gas or vacuum, or by a different force. The driver 48 may be made of any appropriate material.

A drive shaft 52 is connected to the proximal end of the driver 48. As one example, the drive shaft 52 may be a thin-walled tube formed of polyetheretherketone (PEEK) plastic or other suitable material, which is connected at one end to a portion of the proximal end of the driver 48 and at the other end to the control unit 8. When the drive shaft 52 rotates, it causes the threaded driver 48 to rotate as well. This rotation of the threaded driver 48 advances it relative to the correspondingly-threaded guide 50. Alternately, the drive shaft 52 is a tube that transmits compressed gas or vacuum to the driver 48. Alternately, the drive shaft 52 transmits force to the driver 48 in a different way.

An interface 47 is connected to or formed into the cutter 40 at its proximal end. Alternately, the interface 47 is positioned at a different location on the cutter 40. The interface 47 is shown connected to the upper portion of the proximal end of the cutter 40, but could be located to the lower portion or on either side of the proximal end of the cutter 40 instead. The interface 47 is configured to engage the driver 48. As one example, the driver 48 may be a threaded rod or screw, and the interface 47 includes a correspondingly-threaded opening therein. The opening may extend completely through the interface 47. As another example, both the driver 48 and the interface 47 are unthreaded, and the driver 48 is urged relative to the interface 47 under the influence of compressed gas or vacuum, or by a different force. Both the interface 47 and the driver 48 may be made of any appropriate material.

The cutter 40 may be biased downward, such as by a spring 58 held in place by a bracket 62. The spring 58 may be connected to the bracket 62. The spring 58 is configured to exert a downward force on the cutter 40. That is, the spring 58 is in compression, such that it biases the cutter 40 downward. This biasing is performed during substantially all of the travel of the cutter 40. Alternately, the cutter 40 is only biased downward during a portion of the travel of the cutter 40. Alternately, the cutter 40 may be biased upward.

The anastomosis tool 36 also includes a staple holder 18. The staple holder 18 is moveable relative to the anvil 38, between an open position and a closed position. The staple holder 18 is configured to hold staples (not shown). For the purpose of describing the operation of the effector 4, the staples are substantially as disclosed in U.S. patent application Ser. No. 10/309,519 filed on Dec. 4, 2002, "Anastomosis Staple." The staple holder 18 is operationally connected to the control unit 8 non-rigidly, such as by a cable 70.

The anastomosis tool 36 is connected to a mount 30 to form an assembly 28. The mount 30 may include two spaced-apart members 31 connected at their proximal ends to a cross member 33, forming an open-ended configuration. The cross member 33 may be at a substantially right angle to at least one of the members 31, or may be oriented at a different angle to at least one of the members 31. The mount 30 may be a unitary structure, wherein the members 31 and cross member 33 form an integral unit. The members 31 and the cross member 33 all lie in substantially the same plane. Alternately, the members 31 and the cross member 33 do not all lie in substantially the same plane. The mount 30 may be constructed from stainless steel or other suitable biocompatible material or materials.

The tool 36 may be connected to the mount 30 via an interface mechanism 32. The interface mechanism 32 is compliant, and may be a spring, such as a leaf spring, or other mechanism that is at least partially elastic or flexible. Alternately, the interface mechanism 32 may be substantially rigid. Alternately, the interface mechanism 32 may include additional parts, structures or mechanisms to connect the tool 36 to the mount 30 in an appropriate manner. The interface mechanism 32 structure may be movable relative to the mount 30. Where the interface mechanism 32 is moveable substantially linearly relative to the mount 30, the compliance of the interface mechanism 32 may be lower in the linear direction of motion and higher in a direction perpendicular to or otherwise angled away from the linear direction of motion.

Figure 6:
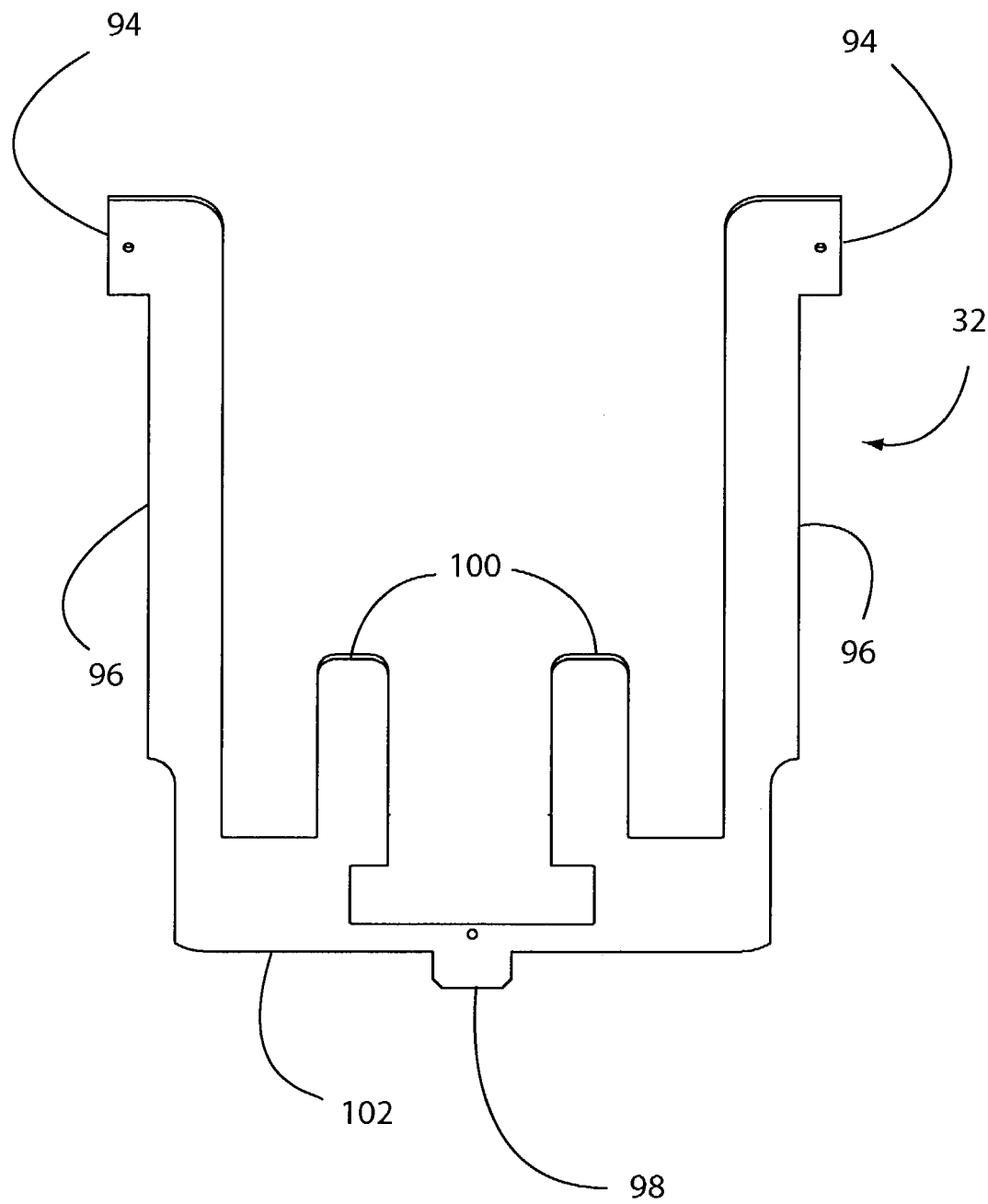
FIG. 6 is a top view of a spring utilized in the effector of FIG. 4.
Figure 10:
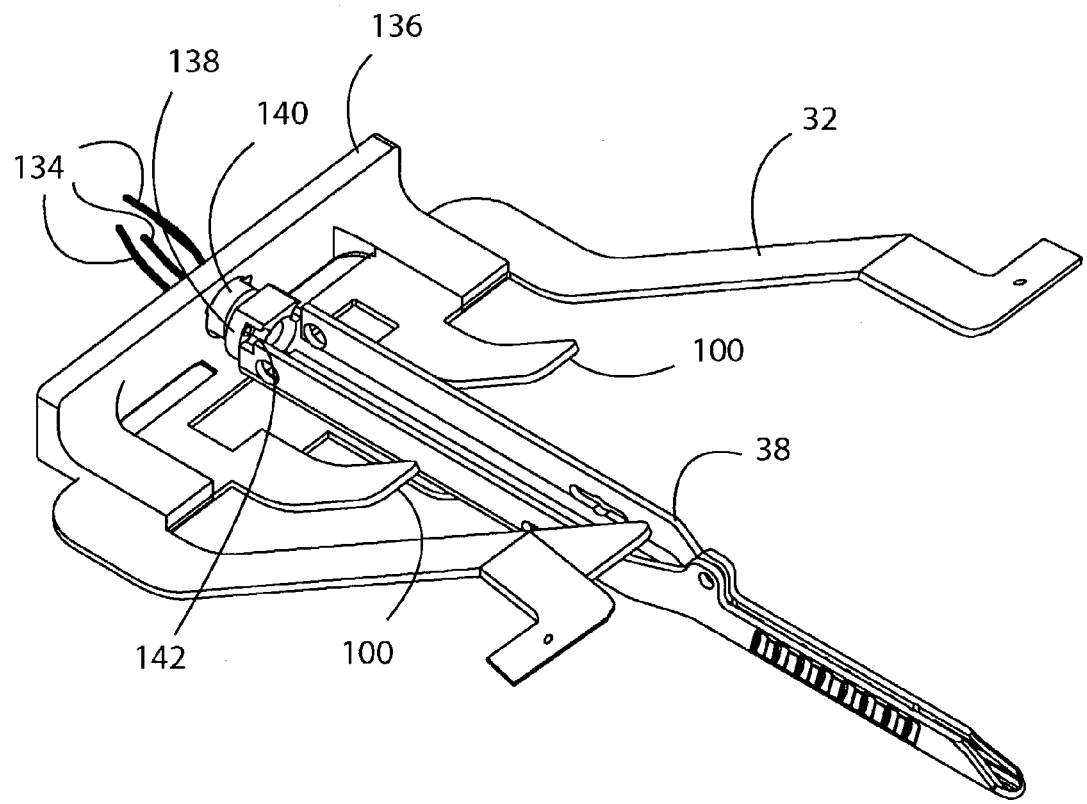
FIG. 10 is a perspective view of an embodiment of a portion of the effector of FIG. 4.

Referring also to FIG. 6, an exemplary embodiment of an interface structure 32 utilized with an anastomosis tool 36 is shown. The interface structure 32 is a leaf spring, advantageously is composed of nickel-titanium alloy or other superelastic alloy, at least in part. Alternately, the interface structure 32 is constructed from stainless steel or other suitable biocompatible material having an appropriate spring constant. The interface structure 32 includes two arms 96. Alternately, the interface structure 32 includes one arm 96, or more than two arms 96. A proximal segment 102 of the leaf spring 32 connects the arms 96 to one another. Advantageously, the leaf spring 32 is unitary, with the arms 96 and the proximal segment 102 being components thereof. A tab 98 extends proximally from the proximal segment 102, at approximately the center of the proximal segment 102. The tab 98 may be positioned differently relative to the proximal segment 102, if desired. In addition, at least one tongue 100 may extend distally from the proximal segment 102 of the interface structure 32. Referring also to FIG. 10, the tongue or tongues 100 may engage the staple holder 18

(not shown) and bias it to an open position relative to the anvil 38. The tongue or tongues 100 of the leaf spring 32 may be connected in any appropriate manner to the anastomosis tool 36, such as by welding, adhesive, connectors, or any other or additional structure, mechanism or method. Alternately, the anastomosis tool 36 is connected also, or instead, to a different part of the leaf spring 32.

At least one arm 96 of the interface structure 32 has a distal end 94 that is oriented substantially laterally and connected to a corresponding slider 34. The connection between the distal end 94 of an arm 96 and the slider 34 may be accomplished with any appropriate structure, mechanism or method. For example, the distal end 94 of an arm 96 may be pressure-fit into a slot (not shown) on a side of the corresponding slider 34; welded to the corresponding slider 34; attached with adhesive to the corresponding slider 34, or otherwise connected thereto. Alternately, a different part of each arm 96 is connected to a corresponding slider 34, or the distal end 94 of at least one arm 96 is configured differently and attached to the corresponding slider 34.

An actuator 44 may extend into each passage 35 within the mount 30. Each actuator 44 may be connected to the corresponding slider 34, directly or operatively, in any appropriate manner. Each actuator 44 may be any suitable mechanism or structure for transmitting force. As an example, each actuator 44 may be a threaded drive screw. A portion of each slider 34 may include a threaded surface 37. A portion of the surface of at least one passage 35 instead, or additionally, may include a threaded surface. Each threaded surface 37 is shaped and threaded to match the size, shape and threading of the corresponding actuator 44. Rotation of the actuator 44 causes the corresponding slider 34 to move proximally or distally, depending on the direction of rotation of the actuator 44. This motion may be caused by direct engagement between the actuator 44 and a threaded surface 37 of the corresponding slider 34. Alternately, where the passage 35 is threaded at least partially, the distal end of the actuator 44 may press the corresponding slider 34 distally as the actuator 44 advances.

A flexible drive shaft 45 is connected to the proximal end of each actuator 44. As one example, at least one drive shaft 45 may be a thin-walled tube formed of PEEK plastic or other suitable material, which is connected at one end to a portion of the proximal end of the corresponding actuator 44 and at the other end to the control unit 8. When the drive shaft 45 rotates, it causes the corresponding threaded actuator 44 to rotate as well. This rotation of the threaded actuator 44 advances it relative to the correspondingly-threaded passage 35 in the corresponding member 31. Alternately, the drive shaft 45 is a tube that transmits compressed gas or vacuum to the actuator 44. Alternately, the drive shaft 45 transmits force to the actuator 44 in a different way. Alternately, a single drive shaft 45 engages all of the actuators 44, such as by a gear assembly (not shown).

Optionally, a ledge 43 extends distally from the cross member 33 of the mount 30. The ledge 43 may be formed into the cross member 33, or connected to the cross member 33, such as by welding, adhesive, one or more fasteners, or any other appropriate structure, mechanism or method. For example, a bracket 42 may include the ledge 43, where the bracket 42 is attached to the cross member 33.

Figure 7:
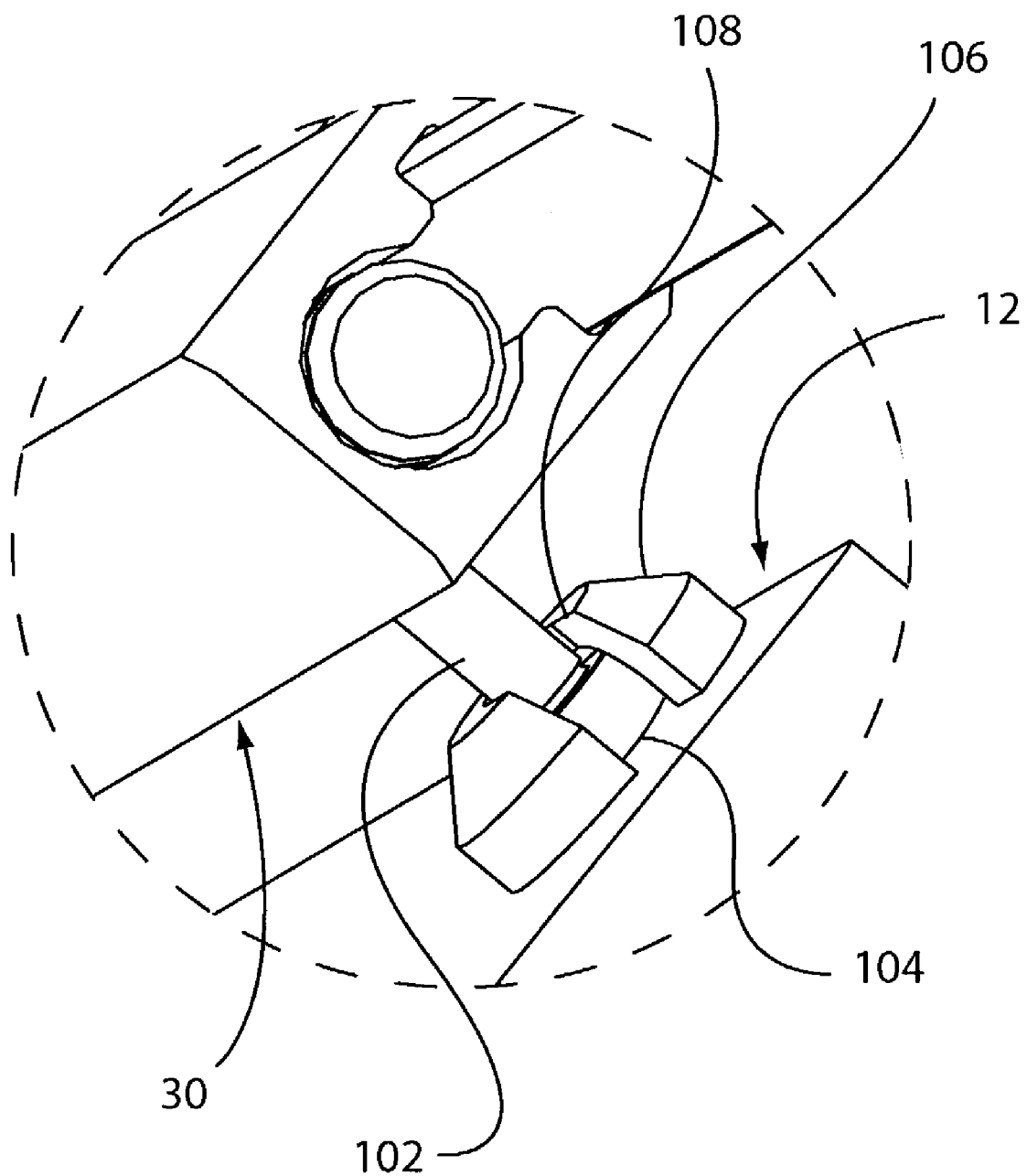
FIG. 7 is a detail perspective view of the connection between the base and a mount of FIG. 4.

The mount 30 may be connected to the base 12 in any appropriate manner. Referring to FIG. 7, an exemplary connection between the mount 30 and the base 12 is shown. Three posts 102 extend downward from the mount 30. A ball 104 is formed into or connected to the bottom of each post 102. A receiver 106 corresponds to each post 102, and is configured to receive the ball 104 of the corresponding post 102. Each receiver 106 is connected to the base, such as by adhesive, welding, one or more fasteners, or any other appropriate mechanism, structure or method.

Each ball 104 is free to rotate relative to the corresponding receiver 106. Thus, each post 102 is free to pivot relative to the corresponding receiver 106, limited by contact between the post 102 and the opening 108 at the top of the receiver 106 through which the post 102 extends. The three balls 104 define a plane, relative to which the base 12 can curve. Alternately, more or fewer than three balls 104 and posts 102 are utilized. Alternately, the posts 102 extend upward from the base 12, and the receivers 106 are connected to the mount 30.

Optionally, the mount 30 is instead connected to the base 12 via a stage (not shown) or other mechanism that is movable relative to the base 12. The stage may be configured to move with one or more degrees of freedom relative to the base 12 to provide more controllability of the orientation of the mount 30 relative to the base 12. Alternately, the mount 30 is rigidly connected to the base 12.

Figure 9:
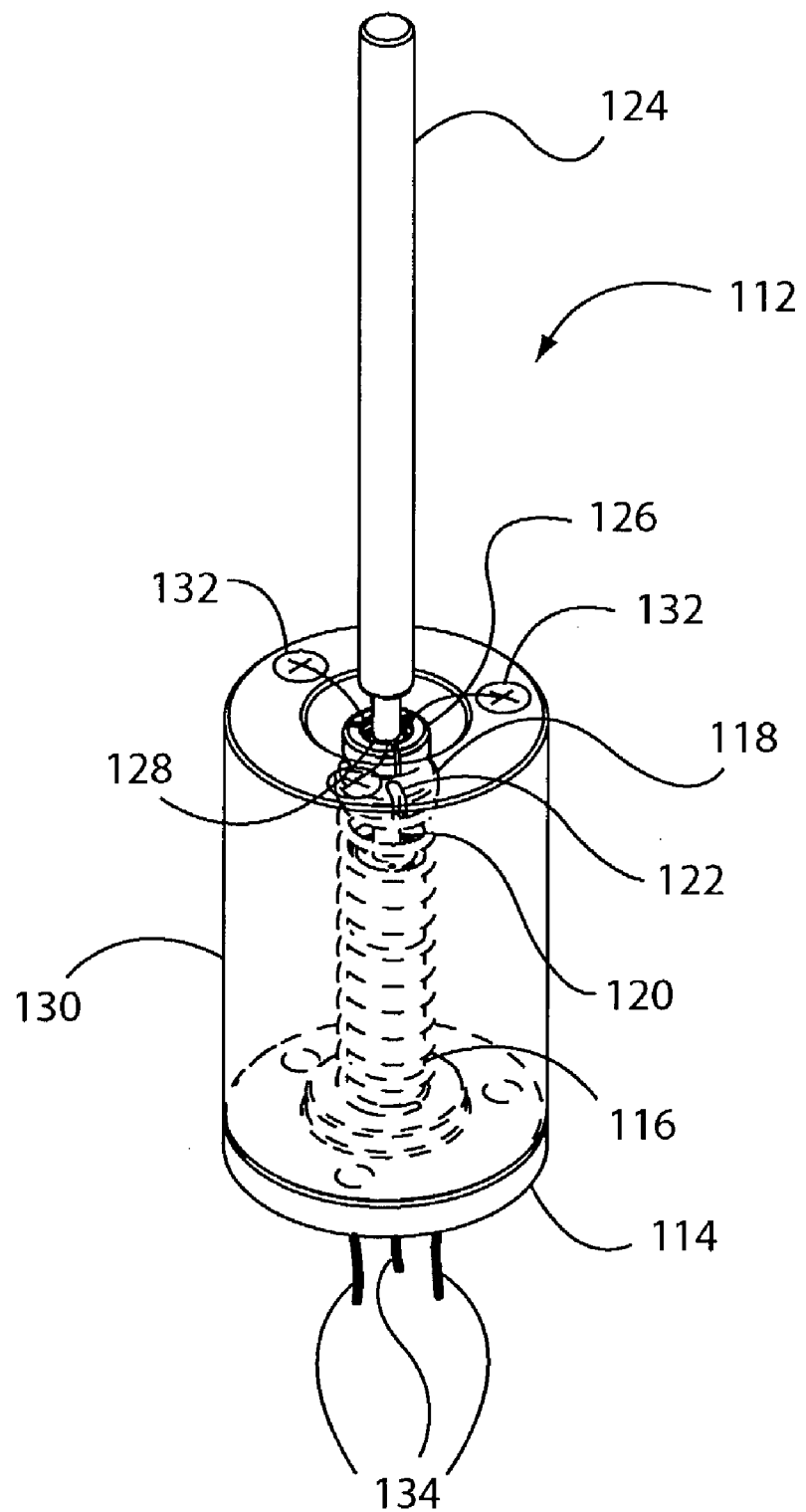
FIG. 9 is a perspective view of an anvil control mechanism optionally utilized in the system of FIG. 1.

Optionally, the anvil 38 and/or the anastomosis tool 36 or other tool 36 may be steerable. Referring to FIG. 9, an anvil control 112 is shown. The anvil control 112 may be a part of the control unit 8, or may be separate from the control unit 8. The anvil control 112 includes a base 114 from which a pylon 116 extends substantially upward. The base 114 may be substantially disc-shaped, and the pylon 116 may be substantially cylindrical. However, the base 114 and/or pylon 116 may be shaped differently. The pylon 116 is substantially centered on the base 114, but may be positioned differently relative to the base 114. Alternately, the base 114 is not a separate component, but instead is a portion of the control unit 8.

A pedestal 118 is connected to the top of the pylon 116 in such a manner that it can bend relative to the longitudinal centerline of the pylon 116. For example, the pedestal 118 may be connected to the pylon 116 via a flexible shaft 120. As another example, the pedestal 118 may be gimbaled relative to the pylon 116. The pedestal 118 may include one or more notches 122 along its perimeter. A joystick 124 is connected to the pedestal 118, such as through a joystick base 126. The joystick base 126 may be positioned immediately adjacent to the pedestal 118, or spaced apart from the pedestal 118 and connected thereto via a post or other intermediate structure. The joystick 124 is connected to the pedestal 118 in such a way that the joystick 124 and the pylon 116 substantially share a longitudinal centerline. Alternately, the joystick 124 may be offset from the pylon 116. The joystick base 126 may include one or more notches 128 along its perimeter. A shell 130, shown in FIG. 9 with phantom lines, is cylindrical, with a cavity at its center. The shell 130 is connected to the base 114 such that the pylon 116 extends into the cavity of the shell 130. The shell 130 includes one or more passages 132 longitudinally therethrough, extending substantially parallel to the longitudinal centerline of the pylon 116. Alternately, the passages 132 are oriented differently. Alternately, the shell 130 is configured differently.

At least one cable 134 extends through each passage 132 in the shell. Each cable 134 may be made of stainless steel or any other appropriate material. Each cable 134 is connected to the joystick 124 directly or indirectly. For example, each cable 134 extends through the corresponding passage 132, out of the proximal end of the passage 132, then radially toward the joystick base 126. At the joystick base 126, each cable 134 then passes through a notch 128 therein, which is narrow enough to hold the cable 134 firmly therein. Each cable 134 then extends distally through a notch 122 in the pedestal 118, and is anchored to the pedestal 118 by any appropriate structure, mechanism or method. For example, a bead (not shown) or similar structure may be fixed to the cable 134, where the bead is larger than the notch 122 in the pedestal 118, such that the bead cannot be pulled through the notch 122. As another example, each cable 134 may be fixed to the pedestal, such as by welding, soldering or adhesive. Any other structure, mechanism or method may be used to connect each cable 134 to the pedestal 118.

The anvil control 112 is part of the control unit 8 or otherwise configured such that it is spaced apart from the effector 4. Each cable 134 extends from the anvil control 112 to the effector 4. Referring also to FIG. 10, the anvil 38 is connected to a bracket 136, which in turn is connected to the interface mechanism 32. An interface ring 138 is connected to the bracket 136 by a ball joint 140, and the anvil 38 is connected to the interface ring 138. The interface ring 138 may be shaped differently, if desired. The interface ring 138 includes one or more apertures 142 therein, where the number of apertures 142 is equal to the number of cables 134. Each cable 134 passes through the corresponding aperture 142 and is then anchored to the interface ring 142 by any appropriate structure, mechanism or method. Alternately, the apertures 142 are not used, and the cables 134 are connected to the interface ring 138 differently. Alternately, the numbers of apertures 142 and cables 134 may be different.

The apertures 142 are advantageously spaced substantially evenly about the interface ring 138. The notches 128 are spaced substantially evenly about the joystick base 126, in a similar manner to the spacing of the apertures 142 about the interface ring 138. As the joystick 124 is moved through a range of motion that is substantially conical, the cables 134 connected to the joystick base 126 are selectively tensioned and loosened. This tensioning and loosening of selected cables 134 transmits force to the interface ring 138. This force moves the interface ring 138, and thus moves the anvil 38 to a position analogous to that of the joystick 124. In this way, the anvil 38 is steerable by the anvil control 112. In this embodiment, where the anvil 38 is connected to the mount 30, the staple holder 37 may be connected to the anvil 38, or may be separated completely from the anvil 38.

Figure 11:
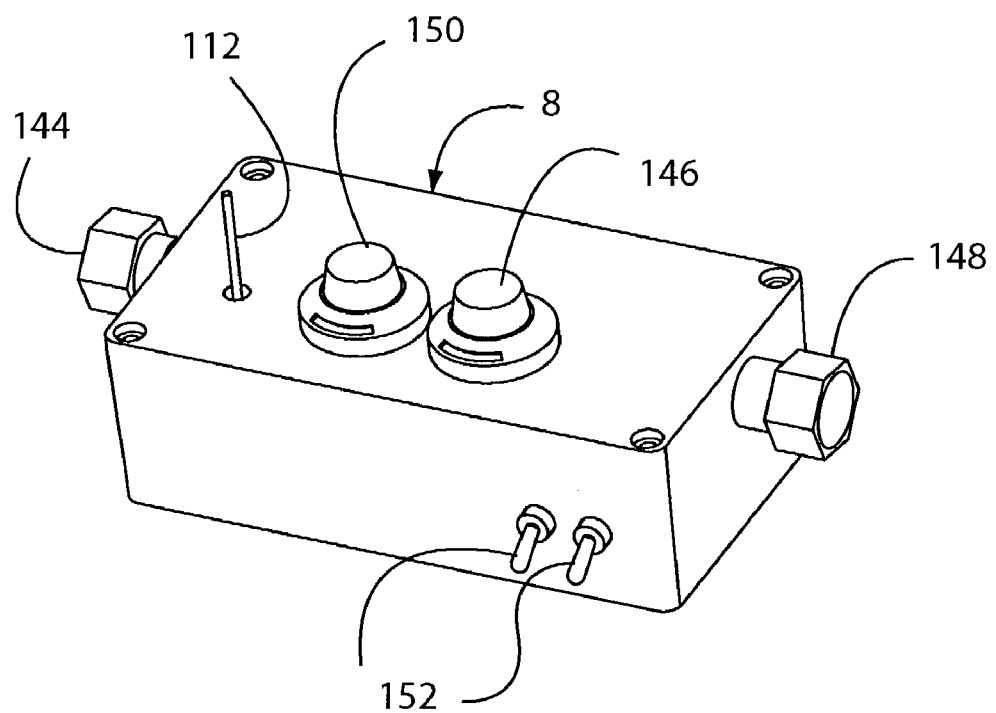
FIG. 11 is a perspective view of a control unit of the system of FIG. 1.

Referring also to FIG. 11, an exemplary control unit 8 is shown. The control unit 8 described here is mechanical. However, the control unit 8 may control the effector 4 via electromechanical actuation, by hardware and/or software control of motors and/or other components, by controlling the pressure and flow of a fluid such as carbon dioxide gas, by a combination of these methods, or by a different method. Further, the control unit 8 may include more, fewer or different controls than described below, where those controls may be configured to perform functions other than those described below. For example, the knobs described below may be any other appropriate control mechanisms. Referring also to FIG. 1, the control unit 8 includes a first knob 144 operationally connected to the effector 4 via a cable 70. The first knob 144 is configured to close the anastomosis tool 36 after the anvil 38 has entered the lumen of a target vessel. The anastomosis tool 36 may be closed by applying tension to a cable 70, where that cable 70 is routed through the anastomosis tool 36 in such a manner that the tension causes the anastomosis tool 36 to close. The control unit 8 also includes a second knob 146 operationally connected to the effector 4 via the drive shaft 52, which extends from the effector 4 to the control unit 8. The second knob 146 is configured to rotate the drive shaft 52 as the second knob 146 is rotated, thereby causing the retraction of the cutter 40 after the anvil 38 has entered the lumen of the target vessel. The control unit 8 includes a third knob 148 that is operationally connected to the effector 4 via a cable 70. The third knob 148 is configured to deploy connectors from the staple holder 18 after the anastomosis tool 36 has been closed. The connectors may be deployed by applying tension to a cable 70, where that cable 70 is routed into the anastomosis tool in such a manner that the tension causes connectors to deploy. The control unit 8 includes a fourth knob 150 that is operationally connected to the effector 4 via a drive shaft 52, which extends from the effector 4 to the control unit. The fourth knob 150 is configured to advance the interface mechanism 32 for insertion of the anvil 38 into a target vessel. The fourth knob 150 does so by rotating the drive shaft or shafts 45, which in turn advances the drive screws 44 as described above. The control unit 8 also includes one or more switches 152 configured to control the vacuum applied to the base 12. One or more vacuum hoses 71 extend from the control unit 8 to the base 12, and the switches 152 are configured to apply vacuum to the base 12 when they are in the open position. The switches 152 may have multiple toggle positions, or may be dials or other controls, such that the amount of vacuum applied can be controlled. The control unit 8 itself is connected to a vacuum source, such as a vacuum connector provided at a hospital operating room, or a vacuum tank, such that the control unit 8 is able to provide vacuum through the one or more vacuum hoses 71. The control unit 8 also includes a joystick 112, configured substantially as described above.

A sheath (not shown) or other structure may collect one or more cables, drive tubes, vacuum hoses and/or wires extending between the effector 4 and the control unit 8, in order to prevent external interference with them, ease insertion through the port in the patient, facilitate the surgical procedure, and improve the aesthetics of the surgical system 2. As an example of the sheath, it may be a flexible tube having one or more lumens extending therethrough, wherein each lumen is configured to receive one or more items extending between the effector 4 and the control unit 8.

An example of the operation of the surgical system 2 will now be described. This example is given in the context of a CABG procedure performed on a beating heart. However, the surgical system 2 may be used to perform a CABG procedure on a stopped heart instead. Further, the surgical system 2 can be used to perform surgical procedures on other organs, and is not limited to the performance of anastomosis, much less a CABG procedure. The sequence of events in the example below is purely exemplary, and may be varied at the discretion of the surgeon. The use of the surgical system 2 does not require delivery of any medical device or tool to the surgical site by a catheter-based delivery system or instrument. That is, no femoral access is required for the use of the surgical system 2. However, a catheter-based delivery system or instrument may be used in conjunction with the surgical system 2 if desired.

Initially, at least one incision is made in the chest of a patient between two adjacent ribs, such that an intercostal approach to the heart may be taken. This incision may be referred to as a port. Alternately, at least one incision is made at a different location on the patient. For example, at least one incision may be made below the rib cage of the patient, such that a sub-xyphoid approach to the heart may be taken. Advantageously, only a single incision is made in the patient, because a separate incision is not needed for an endoscope or other sensor to be inserted into the patient;

rather, the sensor 21 is attached to the effector 4 which will be inserted through the single incision.

The surgeon then makes an incision in the pericardium. The tools and procedures for such an incision are standard. The patient then may be oriented appropriately for the intended anastomosis site. Such orientation may include rolling the patient onto his or her side for better access to the heart. By doing so, the heart naturally moves partially through the incision in the pericardium, facilitating access. For example, if the anastomosis is to be performed on the left side of the heart, the patient may be rolled onto his or her right side; if the anastomosis is to be performed on the right side or back of the heart, the patient may be rolled onto his or her left side.

A measurement device is then inserted through the incision and utilized to measure a graft length between the aorta or other source vessel and the coronary artery having a blockage to be bypassed, while the heart is beating. The measurement device may be a clip that is temporarily attached to the aorta, with a flexible tail attached thereto that is moved to the coronary artery to determine the distance that will be traversed by a graft vessel. Such a measurement device may be substantially as described in U.S. patent application Ser. No. 10/041,542, filed on Jan. 7, 2002, which is hereby incorporated by reference in its entirety. Any other measurement device may be utilized, if desired. Optionally, the surgeon need not physically measure the graft length at all, and instead estimates the length using X-rays, angiograms, visual inspection of the chest cavity, and his or her judgment and experience. The coronary artery that is treated with the surgical system 2 may be the left anterior descending (LAD) artery or any other coronary artery that can be reached through the approach chosen by the surgeon.

Next, a graft vessel is harvested from the patient. The graft vessel may be a saphenous vein, radial artery, or any other appropriate graft vessel. The selection and harvest of a graft vessel is well-known to those skill in the art. The graft vessel is then cut to the graft length determined above. Optionally, a graft vessel is not harvested at all. Rather, a mammary artery is taken down, meaning that one end of a mammary artery is cut and clamped, and the other end of the mammary artery is left in place. The use of the mammary artery simplifies the CABG procedure, because the graft vessel only needs to be connected to the coronary artery, rather than to the coronary artery and the aorta or other source of blood.

The graft vessel is then prepared for anastomosis. This preparation may take place inside the chest cavity, outside the chest cavity, or both. As an example of preparation, one or more flaps are incised in an end of the graft vessel, and those flaps are then connected to the staple holder 18. The connection between the graft vessel and the staple holder 18 is substantially as described in U.S. patent application Ser. No. 10/392,336. The graft vessel may be prepared for anastomosis in any other appropriate way, if desired. Further, where the graft vessel is not already attached to the patient at one end (e.g., a mammary artery), the other end of the graft vessel also can be prepared for anastomosis to the aorta or other blood source.

One of the lungs of the patient may then be deflated, if it has not been deflated already. By deflating one of the lungs, additional working space within the chest cavity is created. The choice of lung for deflation depends on the side of the heart on which the anastomosis is to be performed. For example, where the anastomosis is to be performed on the left side of the heart, the left lung is deflated. Where the anastomosis is to be performed on the right side of the heart, the right lung is deflated.

Optionally, the surface of the deflated lung may be used as a working surface. That is, a portion of the graft vessel, or the effector 4 or one or more tools used to prepare the graft vessel and/or connect it to a target vessel, may be rested temporarily on the surface of the lung during the CABG procedure. A protective element such as a plastic sheet may be placed between the deflated lung and any items rested on the lung.

Optionally, a parameter indicative of pressure in at least one lung may be sensed and utilized to control inflation of at least one lung. For example, at least one pressure sensor (not shown) may be located in a portion of a bifurcated tube (not shown) introduced into the bronchial passages of the patient. Alternately, two separate tubes are utilized, one for each bronchial passage; if so, two separate pressure sensors may be used, one for each tube. The pressure sensor may be connected to the control unit 8 via a wire, a wireless connection, or other structure, mechanism or method. Alternately, the pressure sensor is connected to a mechanism or monitoring device other than the control unit 8. If the pressure changes unexpectedly, the surgeon or anesthesiologist can react to this change and change the ventilation of the patient to prevent over- or under-inflation. The connection between the pressure sensor and the control unit 8 or other mechanism or monitoring device may allow for an automated change of the ventilation of the patient, if desired. As a result, unexpected motion of the lung and/or heart can be reduced or eliminated.

Optionally, the epicardium is dissected at the intended anastomosis site, through the incision in the patient. Such dissection is performed in approximately 30% of all CABG patients, due to the amount of fatty tissue or other tissue present on the exterior of the heart at the anastomosis site. The epicardial dissection procedure is well-known to those skilled in the art. Such dissection may be performed manually, or with a dissection tool (not shown) that is included in the effector 4. Alternately, a second effector 4 is provided, where the tool 36 is a dissection tool. That effector 4 is placed on the heart and actuated in a similar manner to that described below for the actuation of the anastomosis tool 36.

Next, the effector 4 is inserted through the incision in the patient. This insertion may be performed by hand, with a forceps, or with any other appropriate tool or in any other appropriate way. The base 12 of the effector 4 is placed in contact with the exterior of the heart. The surgeon positions the effector 4 in proximity to a coronary artery, and in proximity to the location where the anastomosis between the graft vessel and the coronary artery is to be performed. The coronary artery is referred to as the target vessel with regard to anastomosis.

The base 12 is connected to and rides on the exterior of the beating heart, without substantially restricting the motion of the beating heart. That is, the connection of the base 12 to the exterior of the heart is such that the motion of the heart is substantially unrestricted by the base 12. Further, the shape of the heart and the rate and volume of blood flow through the heart are substantially unaffected by the connection of the base 12 to the exterior of the heart. The patient is stationary on a substantially fixed operating table, gurney or similar structure or mechanism; the base 12 is free to move relative to that operating table or other structure.

When the base 12 is in contact with moving tissue, such as the surface of the beating heart, the base 12 moves along with that tissue. The sensor 21 is substantially fixed relative to the base 12, regardless of whether the sensor 21 is connected directly to the base 12 or whether the sensor mount 22 is used. Because the sensor 21 is substantially fixed relative to the base 12, the sensor 21 also moves along with that tissue. Thus, as the tissue moves and the base 12 and sensor 21 move along with it, the sensor 21 maintains a substantially fixed distance from the tissue, and a substantially fixed orientation relative to that tissue. As a result, the view of the surgical field from the sensor 21 remains substantially steady and motionless. Producing a steady view of the surgical field from the sensor 21 while the sensor 21 and base 12 move with moving tissue may be referred to as "virtual stabilization." Where the sensor 21 is an imaging sensor, the visible image of the surgical field remains substantially steady. That is, by substantially fixing the distance between the sensor 21 and moving tissue such as the exterior of the heart, and by placing the base 12 on a specific location on the moving tissue in such a manner as allows the tissue to move freely, virtual stabilization of the image data obtained by that sensor is obtained without the need to resort to expensive and complex computer-based or mechanical motion compensation. Further, the moving tissue need not be immobilized to obtain virtual stabilization.

Positioning the effector 4 relative to the coronary artery may be performed in any appropriate manner. As one example, the surgeon first coarsely positions the effector 4 relative to the coronary artery, then finely positions the effector 4 relative to the coronary artery. Coarse positioning refers to gross positioning of the effector 4 relative to the coronary artery, and fine positioning refers to detailed positioning of the anastomosis tool 36 relative to the coronary artery. At the end of the coarse positioning, the contact elements 14 may straddle the coronary artery to be acted upon by the effector. Vacuum may be applied to the exterior of the heart through the base 12 before coarse positioning, or between coarse positioning and fine positioning.

As an example of coarse positioning, the surgeon moves the effector 4 with forceps along the exterior of the heart. The surgeon then actuates one or both of the switches 152 on the control unit 8, thereby applying vacuum to the exterior of the heart via the base 12. Alternately, one or both of the switches 152 are actuated before the effector 4 is placed on the exterior of the heart, and the amount of vacuum applied through the base 12 is controlled to a first level. At this first level of vacuum, the base 12 can be moved or slid along the exterior of the heart, while still being held to the exterior of the heart. The base 12 is moved to the desired position, in which the contact elements 14 straddle the coronary artery, in proximity to the anastomosis site. When the base 12 reaches the desired position, the amount of vacuum applied through the base 12 is controlled to a second level, which is greater than the first level. The base 12 is then securely affixed to the exterior of the heart.

The surgeon may use the display 11 to view the exterior of the heart via the sensor 21 and determine whether the base 12 is in the desired position relative to the coronary artery. By using the display, rather than a direct view of the anastomosis site, the incision in the patient may be made as small as possible; it does not need to be large enough to allow visual observation of the anastomosis site.

The surgeon also uses the display 11 to perform fine positioning of the anastomosis tool 36. As an example of fine positioning, the anvil 38 is steerable relative to the remainder of the effector 4, as described above. The surgeon views the surgical field on the display 11 and moves the joystick 112 to steer the anvil 38 to a position in which it is substantially parallel to a portion of the coronary artery. The surgeon then releases the joystick 112, leaving the anvil 38 in place. Optionally, a lock or clamp (not shown) is actuated from the control unit 8, locking the cables 134 into place and providing positive confirmation that the anvil 38 will not move relative to the mount 30 after it has been finely positioned.

The coarse and fine positioning described above is merely exemplary. Such positioning could be performed in a different way. For example, a coarse positioning mechanism and a fine positioning mechanism may be provided, where those mechanisms are connected to one another in series or in parallel. As another example, a coarse positioning mechanism and a fine positioning mechanism may be provided independently from one another. Optionally, coarse and fine positioning are combined into a single step and/or a single mechanism for positioning the anastomosis tool.

After fine positioning is completed, the anvil is positioned close to and oriented substantially parallel to a portion of the coronary artery. Further, the effector 4 is moving along with the motion of the heart.

With the anvil 38 properly positioned, the anastomosis procedure can begin. The surgeon actuates the fourth knob 150, thereby actuating the drive screws 44 and urging them distally. As described above, this motion of the drive screws 44 urges the interface mechanism 32 distally, such as by interacting with threads on corresponding sliders 34. The tab 98 of the interface mechanism 32 initially is in contact with the ledge 43 of the mount 30. Where the interface mechanism 32 is a spring, it is in compression initially; the contact between the tab 98 and the ledge 43 prevents the interface mechanism 32 from moving downward. As the interface mechanism 32 moves distally, the tab 98 moves out of contact with the ledge 43. At that time, the interface mechanism 32 is released from compression and moves downward and distally. The motion of the interface mechanism 32 is controlled by selecting its shape and the amount of compression applied to it. Motion of the interface mechanism impels the distal end of the anvil 38 through the wall of the coronary artery and into the lumen of the coronary artery. Optionally, the cutter 40 is initially in a distally-extended position such that the first incising element 66 contacts the wall of the coronary artery first and facilitates entry of the anvil 38 into the tissue of the wall of the coronary artery. Alternately, the anvil 38 is made to penetrate the wall of the coronary artery in a different way. For example, the anvil 38 may be rested gently on the surface of the coronary artery, and the interface structure 32 is gradually moved relative to the coronary artery until the force exerted on the anvil 38 is substantially equal to the force required to penetrate the coronary artery. At that point, the anvil 38 penetrates the wall of the coronary artery and enters the lumen of that coronary artery.

At this point, a portion of the anvil 38 is present in the lumen of the coronary artery. Optionally, the surgeon may retract the cutter 40 a small amount to protect the wall of the target vessel by withdrawing the first incising element 66 into the anvil 38. This retraction is performed by actuating the second knob 146. The surgeon then closes the anastomosis tool by actuating the first knob 144. The staple holder 18 thus presses the flap or flaps at the end of the graft vessel against the side of the coronary artery. Next, the surgeon actuates the third knob 148 to deploy connectors from the staple holder 18 through the flap or flaps of the graft vessel and into the wall of the coronary artery, securing the graft vessel to the coronary artery. The surgeon then actuates the second knob 146 to rotate the drive shaft 52 and cause the retraction of the cutter 40 after the anvil 38 has entered the lumen of the target vessel. As the cutter 40 moves proximally, the second incising element 68 moves upward, above the upper surface 50 of the anvil 38, and creates an arteriotomy in the wall of the coronary artery, within the perimeter of the end of the graft vessel. Where the second incising element 68 has a proximally-facing cutting edge, that edge facilitates the creation of the arteriotomy as the second incising element 28 moves proximally. As a result, blood can flow between the graft vessel and the coronary artery. Alternately, the incision in the wall of the coronary artery is made prior to or during the deployment of connectors from the staple holder 18. The anastomosis between the graft vessel and the coronary artery is now complete.

Vacuum is released from the base 12 by actuating the switch or switches 152, and forceps or another tool or tools are used to move the effector 4 away from the heart. The effector 4 is moved in such a way that the anvil 38 is slid outward from the coronary artery. As described above, the cross-section of the anvil 38 is small enough that the hole in the coronary artery through which the anvil 38 is removed is self-sealing. The surgeon then removes the effector 4 from the patient. If the proximal anastomosis has not yet been performed, and one is required, the surgeon can then perform that procedure.

Optionally, the effector 4 can be utilized in conjunction with a surgical robot, such as the da Vinci surgical robot of Intuitive Surgical, Inc. or the Zeus surgical robot of Computer Motion. If so, the effector 4 may be connected to an arm or an end effector of the surgical robot, or may be placed on tissue such as the exterior of the heart by a gripper or similar end effector of the surgical robot. Advantageously, the effector 4 is not rigidly connected to the surgical robot, such that the heart is allowed to move freely during the anastomosis procedure, and the data from the sensor 21 is virtually stabilized as described above. In this way, special motion compensation for the manipulators and/or robotic arms is not needed, and the complexity of the manipulators may be reduced. Optionally, the base 12 is not utilized, and the surgical robot may utilize active stabilization to position the anastomosis tool at the desired position relative to the heart. The surgical robot may be configured to perform the control functions that otherwise would have been performed by the control unit 8, such that the control unit 8 can be omitted as a separate mechanism.

Figure 12:
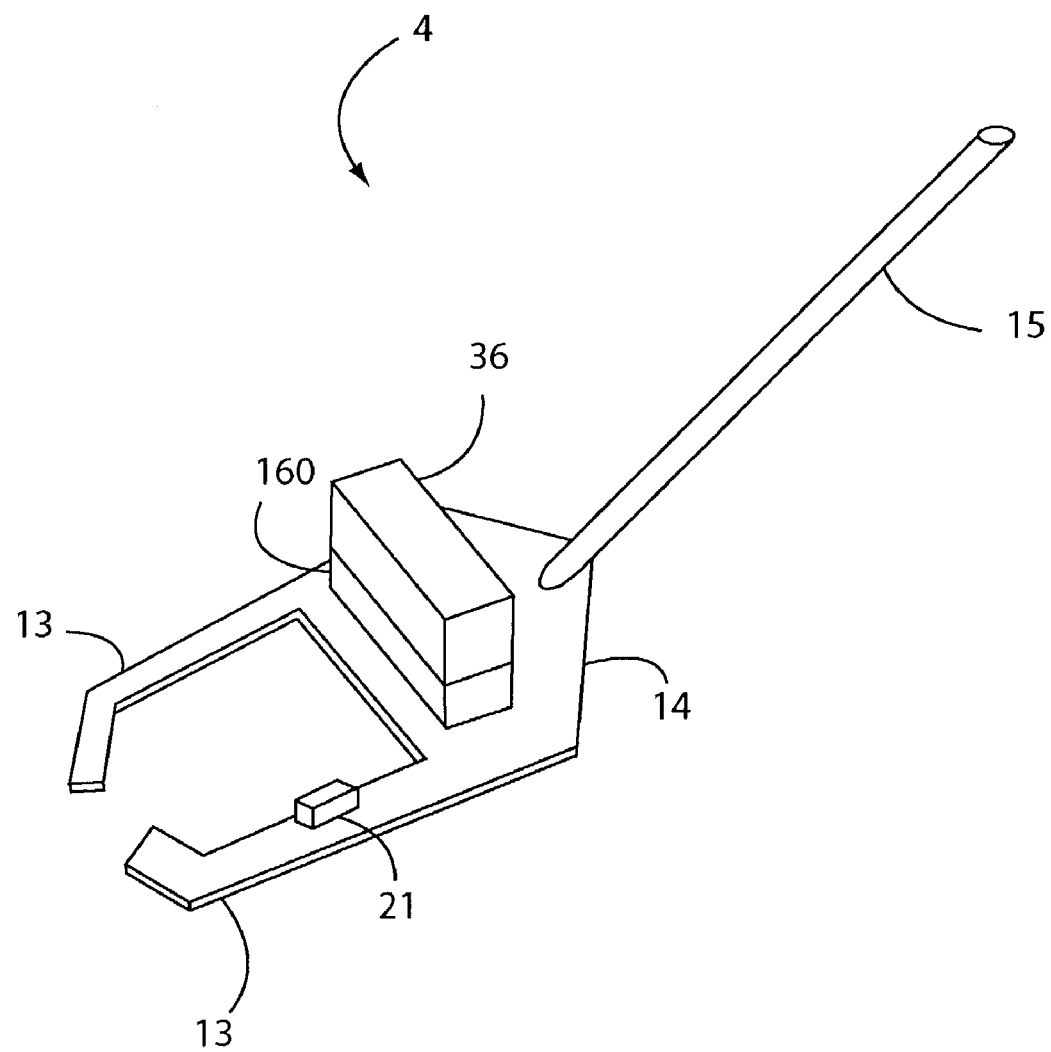
FIG. 12 is a schematic view of a stabilizer used in an alternate embodiment of a minimally-invasive surgical system.

Alternately, referring to FIG. 1, the base 14 is a standard stabilizer, such as disclosed in, for example, U.S. Pat. No. 5,727,569 to Benetti et. al., U.S. Pat. No. 5,894,843 to Benetti et. al., and U.S. Pat. No. 6,511,416 to Green II et. al., all of which are hereby incorporated by reference in their entirety. For clarity and brevity, only the primary differences between the structure and method of use of this alternate embodiment and the embodiment described above are set forth here. A standard stabilizer 14 is at least partially rigid and is substantially rigidly connected to a retractor or other structure or mechanism substantially fixed relative to the patient. For example, the stabilizer 14 may be formed from stainless steel. Vacuum may or may not be applied to tissue through the stabilizer 14. If not, the chambers 24 described above may be omitted. Referring also to FIG. 12, the standard configuration of the stabilizer 14 includes two spaced-apart arms 13 connected substantially rigidly to a standard surgical retractor (not shown) substantially fixed relative to the patient, or connected rigidly to a different structure fixed relative to the patient. An arm 15 connects the stabilizer 14 to the retractor or other structure, where the arm 15 is rigid or is selectively changeable between a non-rigid configuration and a rigid configuration. For clarity, the control unit 8, and the connections between the effector 4 and the control unit 8, are omitted from FIG. 12.

The stabilizer 14 does not move along with the tissue that it contacts or allow substantially unrestricted motion of that tissue. Instead, the stabilizer 14 presses down on the tissue, or lifts up a portion of the tissue, substantially immobilizing the tissue that contacts the arms 13 of the stabilizer 14. This immobilization occurs because the stabilizer 14 is rigidly connected to a fixed object. However, the tissue located between the arms 13 is not immobilized; rather, it is still able to move, albeit to a lesser degree than before contact between the adjacent tissue and the stabilizer 14. For example, where the tissue is heart tissue, and the heart is beating, the beating of the heart against the stabilizer 14 causes tissue to alternately bulge into and move out of, and move laterally within, the space between the arms 13 of the stabilizer 14.

A suspension 160 connects the tool 36 to the stabilizer 14. The suspension 160 allows the tool 36 to move relative to the stabilizer 14, such that it can float relative to the stabilizer 14. In this way, the tool 36 can engage tissue between the arms 13 of the stabilizer 14, or otherwise in proximity to the stabilizer 14, and move along with that tissue, as described in greater detail below. The suspension 160 may be any mechanism or structure configured to allow motion of the tool 36 relative to the stabilizer 14. The suspension 160 may be passive or active. A passive suspension 160 may include at least one spring, such as one or more leaf springs, one or more coil springs, a combination thereof, or other flexible or compliant mechanisms or structures alone or in combination. An active suspension 160 may be connected to the control unit 8, and may include a motor, a drive unit, and/or any mechanism or structure for receiving energy, force and/or control input. At least one sensor 21 may be connected to the stabilizer 14, the tool 36, or both.

The tool 36 may be movable relative to the stabilizer 14 in at least one of three ways. First, at least a portion of the tool 36 is movable in the vertical direction relative to the stabilizer 14, due to the presence of the suspension 160. In this way, after the anvil 38 has entered the lumen of the target vessel, the anvil 38 can move vertically up and vertically down to track the motion of the target vessel, thereby preventing damage to the target vessel. Second, at least a portion of the tool 36 may be movable in rotation relative to the stabilizer 14. As described above, the anvil 38 may be connected to an interface ring 138 that in turn is connected to a ball joint 140, allowing the anvil 38 to rotate relative to the ball joint 140. Third, at least a portion of the tool 36 is configured to move at least partly in a direction toward the target vessel. As described above, the tool 36 is connected to a compliant interface mechanism 32 that moves relative to a mount 30. When the interface mechanism 32 moves to a selected point, it impels the anvil 38 at least partly in a direction toward the target vessel, and urges the distal end of the anvil 38 into the target vessel.

Where the surgical system 2 includes the stabilizer 14, the stabilizer 14 is inserted into the patient through an incision, in the same manner as described above. The incision may be intercostal, sub-xyphoid, or in any other appropriate location relative to the tissue to be treated. Where the system 2 is used to perform a CABG procedure, a sub-xyphoid approach may facilitate access to certain areas of the heart, and an intercostal approach may facilitate access to other areas of the heart.

After the stabilizer 14 is inserted through the incision, it is placed onto tissue such as the heart. The stabilizer 14 then may be rigidly connected to a retractor or other structure fixed relative to the patient. This rigid connection causes the stabilizer 14 to apply pressure to the tissue, substantially immobilizing the tissue in contact with it. Alternately, the stabilizer 14 utilizes vacuum or other means to affix to tissue, then lift upward on the tissue to substantially immobilize it.

The anvil 38 is steered relative to the target vessel, and a portion of the anvil 38 is inserted into the target vessel substantially as described above. After a portion of the anvil 38 has been inserted into the lumen of the target vessel, the staple holder 18 is then moved to a closed position, holding the wall of the target vessel between it and the anvil 38. The tool 36 is thus registered to the anastomosis site, and the suspension 160 allows the tool 36 to move substantially freely with the target vessel. That is, the tool 36 is secured to the target vessel, then floats relative to the stabilizer 14. The anastomosis is performed, and the effector 4 is withdrawn from the patient, in substantially the same manner as described above.

While the invention has been described in detail, it will be apparent to one skilled in the art that various changes and modifications can be made and equivalents employed, without departing from the present invention. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A system for performing anastomosis between a graft vessel and a target vessel, wherein the anastomosis site is accessed through an incision in a patient, and wherein a structure is substantially fixed relative to the patient; the system comprising:
    a stabilizer;
    an anastomosis tool connected to said stabilizer, wherein at least a portion of said anastomosis tool is configured for motion relative to said stabilizer, said anastomosis tool comprising
        a staple holder, and
        an anvil movable relative to said staple holder; and
    a suspension connected to said stabilizer and to said anastomosis tool, wherein said suspension is passive and includes at least one spring.

2. The system of claim 1, wherein said stabilizer is substantially rigidly connected to the structure.

3. The system of claim 1, wherein at least part of said stabilizer is rigid.

4. A system for performing anastomosis between a graft vessel and a target vessel, wherein the anastomosis site is accessed through an incision in a patient and wherein a structure is substantially fixed relative to the patient; the system comprising:
    a stabilizer;
    an anastomosis tool connected to said stabilizer, wherein at least a portion of said anastomosis tool is configured for motion relative to said stabilizer, said anastomosis tool comprising
        a staple holder, and
        an anvil movable relative to said staple holder; and
    a suspension connected to said stabilizer and to said anastomosis tool, wherein said suspension is active.

5. The system of claim 1, wherein said motion includes at least one rotational component.

6. The system of claim 1, further comprising an incising element movable relative to said anvil.

7. The system of claim 1, wherein said anvil is adapted to be biased toward the target vessel.

8. The system of claim 1, wherein said tissue stabilizer further comprises
    a bracket;
    a ball joint connected to said bracket; and
    an interface ring connected to and movable relative to said ball joint;
    wherein said anvil is connected to said interface ring.

9. The system of claim 8, wherein the proximal end of said anvil is connected to said interface ring.

10. The system of claim 8, further comprising at least one cable connected to said interface ring, wherein said at least one cable controls rotational motion of said anvil.

11. The system of claim 1, wherein said motion is at least partly in a direction toward the target vessel.

12. The system of claim 1, wherein said anastomosis tool further comprises a mount connected to said suspension and to said anvil and said staple holder, wherein said mount allows motion of at least a part of said anastomosis tool toward the target vessel.

13. The system of claim 12, wherein said mount includes an interface structure connected to said anastomosis tool, and wherein said interface structure allows motion of at least a part of said anastomosis tool toward the target vessel.

14. The system of claim 13, wherein said interface structure is a leaf spring.

15. The system of claim 13, further comprising at least one actuator connected to said interface structure, wherein each said actuator is configured to urge said interface structure relative to said mount.

16. The system of claim 1, wherein said suspension allows motion at least partly in a direction toward the target vessel.

17. The system of claim 1, further comprising a unitary anastomosis device; wherein said anastomosis tool is configured to deploy said unitary anastomosis device to connect the graft vessel to the target vessel.

18. The system of claim 1, further comprising a plurality of connectors; wherein said anastomosis tool is configured to deploy said connectors to connect the graft vessel to the target vessel.

19. The system of claim 18, wherein said connectors are clips.

20. The system of claim 18, wherein said connectors are staples.

21. The system of claim 18, wherein said connectors are superelastic.

22. The system of claim 18, wherein said connectors are plastically deformable.

* * * * *